United States Patent [19]

Seubert et al.

[11] 4,141,978

[45] Feb. 27, 1979

[54] 2-ACYL-4-OXO-PYRAZINO-ISOQUINOLINE DERIVATIVES AND PROCESS FOR THE PREPARATION THEREOF

[75] Inventors: Jürgen Seubert, Darmstadt; Herbert Thomas; Peter Andrews, both of Wuppertal, all of Fed. Rep. of Germany

[73] Assignee: Merck Patent Gesellschaft mit beschrankter Haftung, Darmstadt, Fed. Rep. of Germany

[21] Appl. No.: 742,133

[22] Filed: Nov. 15, 1976

Related U.S. Application Data

[62] Division of Ser. No. 533,467, Dec. 16, 1974, Pat. No. 4,001,211.

[30] Foreign Application Priority Data

Dec. 17, 1973 [DE] Fed. Rep. of Germany ....... 2362539

[51] Int. Cl.² .................. C07D 241/36; A61K 31/495
[52] U.S. Cl. ..................................... 424/250; 544/344
[58] Field of Search ................. 260/268 TR; 544/344; 424/250

[56] References Cited

U.S. PATENT DOCUMENTS 4,001,411  1/1977  Seubert et al. ................ 260/268 TR
4,049,659  9/1977  Seubert et al. ................ 260/268 TR
4,051,243  9/1977  Seubert et al. ................ 260/268 TR

FOREIGN PATENT DOCUMENTS 1470062  11/1968  Fed. Rep. of Germany.

*Primary Examiner*—Jose Tovar
*Attorney, Agent, or Firm*—Millen & White

[57] ABSTRACT

2-Acyl-4-oxo-hexahydro-4H-pyrazino[2,1-a]isoquinoline derivatives of the formula

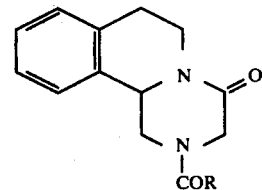

wherein COR is the acyl radical of an up to 26 carbon atom acid and their physiologically acceptable acid addition and quaternary ammonium salts, are anthelmintics and can be produced by reacting 4-oxo-1,2,3,6,7,11b-hexahydro-4H-pyrazino-[2,1-a]isoquinoline with an acid or a reactive functional derivative thereof.

16 Claims, No Drawings

2-ACYL-4-OXO-PYRAZINO-ISOQUINOLINE DERIVATIVES AND PROCESS FOR THE PREPARATION THEREOF

This is a division of application Ser. No. 533,467, filed Dec. 16, 1974, now U.S. Pat. No. 4,001,211.

BACKGROUND OF THE INVENTION

This invention relates to novel 2-acyl-4-oxo-hexahydro-4H-pyrazino[2,1-a]isoquinoline derivatives.

A similar compound, 2-benzoyl-4-oxo-1,2,3,6,7,11b-hexahydro-4H-pyrazino[2,1-a]isoquinoline, has been described as an intermediate in German Offenlegungsschrift No. 1,470,062.

SUMMARY OF THE INVENTION

The 2-acyl-4-oxo-hexahydro-4H-pyrazino[2,1-a]isoquinoline derivatives of this invention are those of the general Formula 1

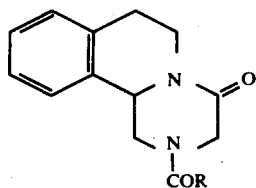

wherein COR is the acyl radical of an up to 26 carbon atom acid, with the proviso that when R is a phenyl group, the benzene ring is substituted, and the physiologically acceptable acid addition and quaternary ammonium salts thereof.

In a composition aspect, this invention relates to the novel compounds of Formula 1. In another composition aspect, this invention relates to pharmaceutical compositions comprising at least one such compound in admixture with a pharmaceutically acceptable carrier. In process aspects, this invention relates to processes for the production of such compounds and to their use as anthelmintics.

For the sake of brevity, the following designations will be employed hereinbelow: "HPI" for the compound "4-oxo-1,2,3,6,7,11b-hexahydro-4H-pyrazino[2,1-a]isoquinoline" and "-HPI" for the radical "-4-oxo-1,2,3,6,7,11b-hexahydro-4H-pyrazino[2,1-a]isoquinoline" lacking the hydrogen atom on the secondary amino nitrogen atom. Accordingly, the compounds of Formula 1 can be designaged generically as "2-acyl-HPI-"

It has been found that the compounds of Formula 1 and their physiologically acceptable salts possess, with good compatibility, parasitological and pharmacological properties. They are effective, inter alia, as valuable anthelmintics with an especially broad spectrum of effectiveness against cestodes and trematodes. Psychotropic and blood-pressure-lowering effects can occur. The compounds of Formula 1 can, therefore, be utilized as drugs in the human and/or veterinary medicine, especially for attaining anthelmintic effects, and also as intermediates for the preparation of other medicinal agents.

Like the racemic compounds of Formula 1, the optical antipodes thereof are likewise effective, particularly those with an optical configuration corresponding to the levorotatory HPI.

Of the 2-acyl-HPI of Formula 1, which include all those wherein the 2-acyl group of any organic carboxylic acid of up to 26 carbon atoms except benzoic acid, preferred are those of Formulae 1a through 1j, which correspond to Formula 1 with the acyl group (—CO—R) having the following values, respectively:

1a. A benzoyl group substituted respectively once in the o-position by fluorine or in the m- or p-position by fluorine, chlorine, nitro, hydroxy, amino, formylamino, acetylamino, pentanoylamino, hexanoylamino, octanoylamino, oleoylamino, methoxyacetylamino, methylamino, dimethylamino, or allylamino;

1b. a cyclopropyl, cyclobutyl, cyclopentyl, cyclohexyl, or cycloheptylcarbonyl group, optionally additionally monosubstituted by, respectively, fluorine, chlorine, nitro, hydroxy, amino, formylamino, acetylamino, pentanoylamino, hexanoylamino, octanoylamino, oleoylamino, methoxyacetylamino, methylamino, dimethylamino, or allylamino;

1c. an alkanoyl group of up to 8 carbon atoms optionally additionally substituted by methoxy or ethoxy;

1d. furyl-2-carbonyl, furyl-3-carbonyl, thienyl-2-carbonyl, thienyl-3-carbonyl, or 2-thienylmercaptomethylcarbonyl;

1e. a 2-, 3-, or 4-pyridylcarbonyl or 2-, 3-, or 4-N-oxidopyridylcarbonyl group, optionally additionally monosubstituted by, respectively, fluorine, chlorine, hydroxy, amino, formylamino, acetylamino, pentanoylamino, hexanoylamino, octanoylamino, oleoylamino, methoxyacetylamino, methylamino, or dimethylamino;

1f. an aminoalkanoyl group (of up to 4 carbon atoms), an aminocycloalkylcarbonyl group (of 6–8 carbon atoms), an aminobenzoyl group, or an aminopyridylcarbonyl group substituted on the N-atom by benzylidene, 2-hydroxybenzylidene, 2-hydroxy-3-methoxybenzylidene, carboxymethylidene, 3-phenyl-2-propenylidene, or furfurylidene;

1g. a phenylazobenzoyl group, the terminal-positioned phenyl residue of which in the p-position is substituted by hydroxy, alkoxy of up to 4 carbon atoms, amino, alkylamino of up to 4 carbon atoms, or dialkylamino of up to 8 carbon atoms, and which can be substituted at the other locations optionally additionally by carboxy, aliphatic acylamino of up to 4 carbon atoms, halogen, sulfo, or alkyl of up to 4 carbon atoms;

1h. an aminocycloalkylcarbonyl group of 6–8 carbon atoms, an aminobenzoyl group, or an aminopyridylcarbonyl group, the amino groups of which are masked by a benzyl group optionally substituted by hydroxy and/or methoxy;

1i. a thiazolyl-, isothiazolyl-, oxazolyl-, or isoxazolylcarbonyl group, optionally additionally substituted by methyl or nitro;

1j. a 2-, 3- or 4-piperidylcarbonyl group substituted on the nitrogen atom by formyl, acetyl, pentanoyl, hexanoyl, octanoyl, oleoyl, methoxyacetyl, carboxymethyl, allyl, benzyl (which can optionally be substituted by hydroxy or methoxy), or 3-phenylpropyl, including the physiologically acceptable acid addition and quaternary ammonium salts, and optical antipodes thereof.

Compounds of Formula 1 of particular importance are those wherein R is cyclohexyl, o-, m- and p-fluorophenyl, p-chlorophenyl, m- and p-aminophenyl, m- and p-formylaminophenyl, p-nitrophenyl and 3-pyridyl, as well as methyl, ethyl, cyclopropyl, cyclobutyl, cyclopentyl, cycloheptyl, m-chlorophenyl, m- and p-hydroxyphenyl, m- and p-methylaminophenyl, m- and p-dimethylaminophenyl, m- and p-acetylaminophenyl, m- and p-methoxyacetylaminophenyl, 2-thienyl, 3-thienyl, thienyl-2-mercaptomethyl, 2-furyl, 2- or 3-pyridyl, 1-oxido-3-pyridinio.

In a process aspect, this invention relates to a process for the preparation of compounds of Formula 1 which comprises:

(a) reacting 4-oxo-1,2,3,6,7,11b-hexahydro-4H-pyrazino-[2,1-a]isoquinoline (HPI) with a compound of Formula 2

R—COOH (2)

wherein R has the values given for Formula 1, or with a functional derivative thereof; or (b) cyclizing a compound of Formula 3

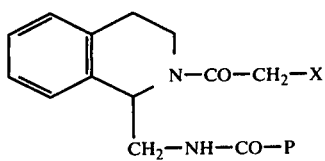

wherein R has the values given for Formula 1 and X is F, Cl, Br, I, methylsulfonyloxy or arylsulfonyloxy of 6–10 carbon atoms, preferably p-toluenesulfonyloxy, in the presence of a cyclizing agent under conditions which split off HX; or (c) treating a compound of Formula 4

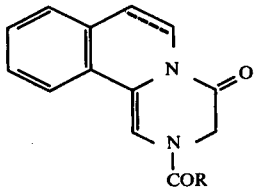

wherein the dashed line means a double bond which can be in the 6,7-position of the ring system, with a reducing agent.

Optionally, the R group of a thus-obtained compound of Formula 1 thereafter is converted into another R group and/or a thus-obtained racemic compound 1 is separated into the optical antipodes thereof and/or that a thus-obtained base of Formula 1 is converted into a physiologically acceptable acid addition salt or a quaternary ammonium salt thereof or a base of Formula 1 is liberated from an acid addition salt thereof.

It will be apparent that in the process of this invention, R can, for example, be hydrogen, alkyl, cycloalkyl, cycloalkylalkyl, aralkyl, aryl or heterocyclic, and in the compounds of Formula 1, R also has these same values, except phenyl.

When R is alkyl, the alkyl group can be straight-chain or branched and can contain, e.g., up to 17, preferably up to 6 carbon atoms. Cycloalkyl groups can contain, e.g., 3–12, preferably 3–7, ring carbon atoms, and a like number of total carbon atoms including those wherein 2 or 3 ring carbon atoms form an endoalkylene bridge. Such cycloalkyl preferably contain a total of up to 8 carbon atoms. Aralkyl groups preferably contain up to 10 carbon atoms and the aryl group is preferably phenyl. Aryl groups can be partially or, in the case of naphthyl, completely hydrogenated and can contain, e.g., a total of up to 10 carbon atoms and 1–2 rings. Heterocyclic groups can contain, e.g., up to 10 ring atoms, up to 15 carbon atoms and 1, 2 or 3 hetero, e.g., O N and/or S ring atoms, and can be joined directly to the carbonyl group by a ring carbon atom or indirectly through a straight-chain or branched-chain alkyl or thia-alkyl group, e.g., of up to 4 carbon atms. Additional double and/or triple bonds can also be contained in the alkyl, cycloalkyl, cycloalkylalkyl, aralkyl, aryl and/or heterocyclic groups. Such groups can also be substituted by one or more conventional groups, e.g., alkyl, alkoxy, halo, nitro.

R preferably is alkyl of up to 8 carbon atoms, which can be substituted by alkoxy of up to 4 carbon atoms; cycloalkyl of up to 7 carbon atoms, which can be substituted by fluorine, chlorine, nitro, amino, alkylamino or dialkylamino wherein each alkyl contains up to 4 carbon atoms, allylamino, benzylamino (which can be substituted by hydroxy and/or methoxy) or aliphatic (optionally also unsaturated) acylamino of up to 18 carbon atoms, a Schiff base blocked amino group, hydroxy or alkoxy of up to 4 carbon atoms; phenyl substituted by one or more of fluorine, chlorine, nitro, amino, alkylamino or dialkylamino of up to 4 carbon atoms in each alkyl group, allylamino, benzylamino (which can be substituted by hydroxy and/or methoxy), aliphatic (optionally also unsaturated) acylamino of up to 18 carbon atoms, Schiff base blocked amino, hydroxy, alkoxy of up to 4 carbon atoms, phenylazo (which can be substituted by hydroxy, methoxy, amino, methylamino, dimethylamino, fluorine, chlorine or lower alkyl), carboxymethylamino or alkoxyacetylamino of up to 4 carbon atoms in the alkoxy group; a thienyl, thienylmercaptomethyl, furyl, thiazolyl, isothiazolyl, oxazolyl isoxazolyl or pyridyl group; or a piperidyl group which can be substituted by alkyl of up to 4 carbon atoms, benzyl or aliphatic (which can be unsaturated) acyl of up to 18 carbon atoms.

The following are illustrative specific R values:

Alkyl, preferably of 1–6 carbon atoms, can be for example: methyl, ethyl, propyl, isopropyl, n-butyl, isobutyl, sec.-butyl, tert.-butyl, n-pentyl, 1-methyl-n-butyl, 2-methyl-n-butyl, isopentyl, 1-ethylpropyl, 1,1-dimethyl-n-propyl, tert.-pentyl, n-hexyl, 1,1-dimethyl-n-butyl, 2,2-dimethyl-n-butyl, isohexyl, n-heptyl, 1,1-dimethyl-n-pentyl, n-octyl, 2-ethylhexyl, also, n-nonyl, 1-(n-butyl)-n-pentyl, n-decyl, u-undecyl, n-dodecyl, n-tridecyl, n-tetradecyl, n-pentadecyl, n-hexadecyl, n-heptadecyl and other isomers thereof, e.g., isodecyl, isododecyl.

Cycloalkyl, preferably of 3–12, more preferably 3–7 carbon atoms, can be, for example, cyclopropyl, cyclobutyl, cyclopentyl, cyclohexyl, cycloheptyl, also cyclooctyl, cyclononyl, cyclodecyl, cycloundecyl and cyclododecyl. Two or three carbon atoms in the cycloalkyl group can be joined together by endoalkylene bridges, for exampl, bridges of 1–8, preferably 1–2 carbon atoms, for example, —CH$_2$— and —CH$_2$—CH$_2$—, as well as —C(CH$_3$)$_2$—, —CH$_2$—CH$_2$—CH$_2$—CH$_2$—, —C(C$_2$H$_5$)$_2$—, —CH(CH$_3$)—CH(CH$_3$)—.

Preferred cycloalkyl groups are bicyclo[2,2,1]heptyl-2, bicyclo[2,2,2]octyl-2, bicyclo[3,2,2]nonyl-2, -3 and -6. Others are bicyclo[4,2,2]decyl-2, -3 and -7, bicyclo[4,3,-2]undecyl-2, -3, -7, -8 and -10, or adamantyl, as well as alkylated bicyclic systems, such as, for example, 7-methylbicyclo[2,2,1]heptyl, 7-ethyl-bicyclo[2,2,1]heptyl, 7,7-dimethyl-bicyclo[2,2,1]heptyl, 7,7-diethylbicyclo[2,2,1]heptyl, 1,7,7-trimethyl-bicyclo[2,2,1]heptyl, 1-methylbicyclo[2,2,2]octyl, or 1,2,3-trimethyl-bicyclo[2,2,2]octyl.

The cycloalkylalkyl groups preferably contain up to 8 carbon atoms and include, for example: cyclobutylmethyl, cyclopentyl-methyl, cyclopentyl-ethyl, cyclohexyl-methyl and cyclohexyl-ethyl.

The alkyl and cycloalkyl groups which contain unsaturated bonds include, for example, ethenyl, ethinyl, 1-propenyl, 2-propenyl, 8-heptadecenyl, 1-cyclopentenyl, 2-cyclopentenyl, 3-cyclopentenyl, 1-cyclohexenyl, 2cyclohexenyl, 3-cyclohexenyl, 1-cycloheptenyl, 2-cycloheptenyl, 3-cycloheptenyl, 4-cycloheptenyl, as well as 1-butenyl, 2-butenyl, 3-butenyl, 1-cyclooctenyl, 2-cyclooctenyl, 3-cyclooctenyl, 4-cyclooctenyl, 5-cyclooctenyl, 1-propinyl and 2-propinyl.

Aralkyl preferably contains up to 10 carbon atoms, with the aryl group being preferably phenyl and the alkyl group being of 1 to 4 carbon atoms including, for example, benzyl, 1- or 2-phenylethyl, 3-phenylpropyl, 1-methyl-1-phenylethyl and 1-methyl-2-phenylethyl.

Aryl group preferably are up to 10 carbon atoms and signifies, for example, substituted phenyl, e.g., tolyl and xylyl, naphthyl-1, or naphthyl-2, as well as phenanthryl-1 (or -2, -3, -4, -9).

The napthyl groups can also be partially or completely hydrogenated and include, for example: 1,2-dihydronaphthyl, 1,2,3,4-tetrahydronaphthyl and decalyl (cis or trans).

Heterocyclic group include, for example, heteroaromatic five- and six-membered systems, which can be condensed optionally with one or two benzo groups and/or a second five- or six-membered heterocyclic ring, preferred such groups including, for example:pyrryl-1 (or -2 or -3), thienyl-2 (or -3), furyl-2 (or -3), indolyl-1 (or -2, -3, -4, -5, -6 or -7), benzofuryl-2 (or -3, -4, -5, -6, or -7), benzothienyl-2 (or -3, -4, -5, -6 or -7), pyridyl-2 (or -3 or -4), α- or γ-pyranyl-2 (or -3 or -4), α- or γ-thiopyranyl-2 (or -3 or -4),quinolyl-2(or -3, -4, -5, -6, -7, or -8), isoquinolyl-1 (or -3, -4, -5, -6, -7 or -8), as well as carbazolyl-1 (or -2, -3, -4 or -9), pyrazolyl-1 (or -3, -4 or -5), imidazolyl-1 (or -2, -4 or -5), benzpyrazolyl-1 (or -2, -4, -5, -6 or -7), benzimidazolyl-1 (or -2, -4 or -5), oxazolyl-2 (or -4 or -5), benzoxazolyl-2 (or -4, -5, -6 or -7), thiazolyl-2 (or -4 or -5), benzthiazolyl-2 (or -4, -5, -6 or -7), isoxazolyl-3 (or -4 or -5), isothiazolyl-3 (or -4 or -5), 1,2,3-triazolyl-1 (or -2 or -4), 1,2,4-triazolyl-1 (or -3 or -5), tetrazolyl-1 (or -2 or -5), 1,2,3- or 1,2,4-oxadiazolyl, 1,2,4-, 1,3,4- or 2,1,5-thiadiazolyl, 2,1,3-benzothiadiazolyl-5, acridinyl-1 (or -2, -3, -4, -5, -6, -7, -8 or -9), pyridazinyl-3 (or -4), pyrimidinyl-2 (or -4 or -5), pyrazinyl, phenazinyl-1 (or -2), phenoxazinyl-1 (or -2, -3, -4 or -9), phenothiazinyl-1 (or -2, -3, -4 or -9), thianthrenyl-1 (or -2), 1,2,5-, 1,2,4- or 1,2,3-triazinyl, 1,2,3,4- or 1,2,4,5-tetrazinyl, purinyl-2 (or -6, -7, -8 or -9), pyrazolo[3,4-d]pyrimidinyl-2 (or -6, -7 or -9), pteridinyl, cinnolinyl-3 (or -4, -5, -6, -7 or -8), phthalazinyl-1 (or -5 or -6), quinazolinyl-2 (or -4, -5, -6, -7 or -8), quinoxalinyl-2 (or -5 or -6), 1,5-naphthyridinyl-2 (or -3 or -4) or nalidixinyl. The heterocyclic groups can also be partially or completely hydrogenated and preferably are 1,4-dioxanyl, morpholinyl, pyrrolidinyl, tetrahydrofuryl, tetrahydrothienyl, pyrazolidinyl, imidazolidinyl, 1,2,3,4-tetrahydropyridyl, 1,2,5,6-tetrahydropyridyl, piperidyl, tetrahydropyranyl, 1,2,3,4-tetrahydroquinolyl, 1,2,3,4-tetrahydroisoquinolyl, hexahydropyridazinyl, hexahydropyrimidinyl or piperazinyl; as well as 1,3-dioxanyl, pyrrolinyl, dihydrofuryl, pyrazolinyl, imidazolinyl, oxazolinyl, oxazolidinyl, thiazolinyl, thiazolidinyl, isoxazolidinyl, isothiazolinyl, isothiazolidinyl, 2,3-dihydrobenzthiazolyl, 1,2-dihydroquinolyl, 3,4-dihydroquinolyl, 1,2-dihydroisoquinolyl, 3,4-dihydroisoquinolyl, decahydroquinolyl, decahydroisoquinolyl, chromenyl, chromanyl, dihydropyridazinyl, tetrahydropyridazinyl, dihydropyrimidinyl, tetrahydropryrimidinyl, dihydropryazinyl, tetrahydropyrazinyl or 1,4-thiazinyl.

These alkyl, cycloalkyl, cycloalkylalkyl, aralkyl, aryl, and heterocyclic groups optionally can be mono- and polysubstituted, including those having several substituents on one carbon atom, including substituents in the cis- or trans-position. Suitable substituents are, for example, one or more of:

Alkyl of up to 4 carbon atoms, preferably methyl or ethyl, as well as n-propyl, isopropyl, n-butyl, isobutyl, sec.-butyl or tert.-butyl; haloalkyl of up to 4 carbon atoms, for example, fluoromethyl, trifluoromethyl or chloromethyl; hydroxyalkyl of up to 4 carbon atoms, e.g., hydroxymethyl or hydroxyethyl, aminoalkyl of up to 4 carbon atoms, and corresponding mono- and dimethyl- as well as mono- and diethylamino groups, preferably aminomethyl, methylaminomethyl, dimethylaminomethyl, methylaminomethyl, dimethylaminoethyl, as well as ethylaminomethyl, diethylaminomethyl, ethylaminoethyl, diethylaminoethyl, methylamino-n-propyl, dimethylamino-n-propyl, diethylamino-n-butyl, etc.; aryl of 6–10 carbon atoms, preferably phenyl; aralkyl of 7–19 carbon atoms, preferably benzyl, as well as triphenylmethyl; halogen, preferably fluorine or chlorine, as well as bromine and iodine; hydroxy; alkoxy of up to 4 carbon atoms, preferably methoxy or ethoxy, as well as n-propoxy, isopropoxy, n-butoxy, isobutoxy, sec.-butoxy or tert.-butoxy; acyloxy of up to 4 carbon atoms, e.g, formyloxy, acetoxy or propionyloxy; substituted acetoxy, e.g., trifluoroacetoxy or methoxyacetoxy; aryloxy of 6–10 carbon atoms, preferably phenoxy; substituted aryloxy, e.g., o-, m- or p-fluorophenoxy, o-, m- or p-chlorophenoxy, o-, m- or p-aminophenoxy, o-, m- or p-methylaminophenoxy, o-, m- or p-dimethylaminophenoxy, o-, m- or p-formylaminophenoxy or o-, m- or p-acetylaminophenoxy; amino; alkylamino of up to 4 carbon atoms, preferably methylamino, ethylamino, as well as n-propylamino, isopropylamino, n-butylamino, isobutylamino., sec.-butylamino or tert.-butylamino; dialkylamino with alkyl groups each of up to 4 carbon atoms, preferably dimethylamino, diethylamino, or methylethylamino, as well as methyl-n-propylamino, methylisopropylamino, methyl-n-butylamino, ethyl-n-propylamino, ethylisopropylamino, ethyl-n-butylamino, di-n-propylamino, diisopropylamino or di-n-butylamino; trialkylammonium with alkyl groups each of up to 4 carbon atoms, e.g., trimethylammonium, triethylammonium; alkenylamino of up to 4 carbon atoms, e.g., vinylamino, 1-propenylamino, allylamino, 1-butenylamino, 2-butenylamino or 3-butenylamino; aralkyl optionally substituted by OH, OCH$_3$, NHCH$_3$, N(CH$_3$)$_2$, SCH$_3$, CH$_3$ and/or C$_2$H$_5$, for example, benzylamino, 2-hydroxybenzylamino, 2-hydroxy-3-methoxybenzylamino; acylamino of up to 18 carbon atoms, wherein acyl is that of a saturated or unsaturated fatty acid, preferably a fatty acid of 1–18 carbon atoms, e.g., formylamino, acetylamino, propionylamino, butyrylamino, pentanoylamino, hexanoylamino, heptanoylamino, octanoylamino, decanoylamino, dodecanoylamino, palmitoylamino, stearoylamino, oleoylamino, linoloylamino, linolenoylamino; acylamino wherein the acyl radical is that of trifluoroacetic acid or a lower-alkoxyacetic acid (alkoxy of 1–4 carbon atoms), e.g., trifluoroacetylamino, methoxyacetylamino, ethoxyacetylamino, propoxyacetylamino, isopropoxyacetylamino, butoxyacetylamino, tert.-butoxyacetylamino; acylamino wherein acyl is the acyl radical of a dicarboxylic acid (of 4–8 carbon atoms) which can form cyclic anhydrides, for example, 3-carboxypropionylamino (succinoylamino), 3-carboxy-cis-prop-2-enylamino (maleinoylamino), 2-carboxycyclopentylcarbonylamino, 2-carboxycyclohexylcarbonylamino, phthaloylamino, 2- or 3-carboxypyridyl-3- or -2-carbonylamino, 3-(carboxyethylmercapto)-propinoylamino; sulfamino; hydroxycarbonylamino substituted by an organic radical of up to 15 carbon atoms, e.g., ethoxycarbonylamino, tert.-butoxycarbonylamino, benzyloxycarbonylamino or 3,5-dimethoxybenzyloxycarbonylamino, as well as cyano-tert.-butoxycarbonylamino, 2-biphenylyl-(4)-isopropoxycarbonylamino, 2,2,2-trichloroethoxycarbonylamino, fluorenyl-(9)-methoxycarbonylamino, p-nitrobenzyloxycarbonylamino, p-chlorobenzyloxycarbonylamino, p-phenylazobenzyloxycarbonylamino, p-(p-methoxyphenylazo)benzyloxycarbonylamino and cyclopentyloxycarbonylamino; alkylidene- or aralkylideneamino of up to 9 carbon atoms, such as, e.g., benzylideneamino, p-methylbenzylideneamino, o-hydroxybenzylideneamino, p-methoxybenzylideneamino, 3,4-dimethoxybenzylideneamino, 2-hydroxy-3-methoxybenzylideneamino, isopropylideneamino, sec.-butylideneamino, carboxymethyleneamino, 3-phenyl-2-propen-1-ylideneamino, furfurylideneamino and 5-nitrofurfurylideneamino; sulfo and disulfo groups formed by the addition of bisulfite to the last-mentioned groups, e.g., α-sulfobenzylamino, α-sulfo-2-hydroxybenzylamino, α-sulfo-2-hydroxy-3-methoxybenzylamino, sulfomethylamino, 1-sulfoethylamino, 1-sulfo-1-carboxymethylamine, (1,3-disulfo-3-phenyl)-propylamino; phenylazo (preferably p-substituted) or naphthylazo-1 or -2 substituted by hydroxy, alkoxy or up to 4 carbon atoms (e.g., methoxy or ethoxy), amino, alkylamino of up to 4 carbon atoms (e.g., methylamino or ethylamino) and/or dialkylamino of up to 8 carbon atoms, (e.g., dimethylamino or diethylamino), which three groups can optionally also be substituted by carboxy, lower alkoxycarbonyl (e.g., methoxycarbonyl and ethoxycarbonyl), acylamino of up to 4 carbon atoms (e.g., formylamino and acetylamino), halogen (e.g., fluorine, chlorine and bromine), sulfo, alkoxysulfonyl (e.g., methoxysulfonyl and ethoxysulfonyl) and/or alkyl of up to 4 carbon atoms (e.g., methyl, ethyl, propyl, isobutyl, tert.-butyl); for example, 3-carboxy-4-hydroxyphenylazo, 4-dimethylaminophenylazo, 4-diethylaminophenylazo, 2-methyl-4-hydroxyphenylazo, 4-methoxy- or 4-ethoxyphenylazo; an amino group blocked by a mono- or disaccharide radical containing 5–12 carbon atoms, preferably a monosaccharide whose hydroxy group on the number 1 carbon atom and/or on the end-position carbon atom oxidized to the carboxylic acid, preferably gluconoylamino, glucuronoylamino, saccharoylamino, galactonoylamino, galacturonoylamino, mucoylamino, mannonoylamino, manno-saccharoylamino, arabinonoylamino and ribonoylamino, as well as maltobionoylamino, lactobionoylamino and saccharobionoylamino; mercapto; alkylmercapto of up to 4 carbon atoms, preferably methylmercapto and ethylmercapto, as well as n-propylmercapto, isopropylmercapto, n-butylmercapto, isobutylmercapto, sec.-butylmercapto and tert.-butylmercapto; arylmercapto of 6–10 carbon atoms, preferably phenylmercapto; acylmercapto of up to 4 carbon atoms, e.g., formylmercapto, acetylmercapto and propionylmercapto; thienyl-2-mercapto; and thienyl-3-mercapto; nitro; cyano; carboxy, alkoxycarbonyl of up to 4 carbon atoms in the alkoxy group preferably methoxycarbonyl and ethoxycarbonyl, as well as n-propoxycarbonyl, isopropoxycarbonyl, n-butoxycarbonyl, isobutoxycarbonyl, sec.-butoxycarbonyl, or tert.-butoxycarbonyl; hydrazino; alkyl- or arylhydrazino, such as 1-methylhydrazino, 2-methylhydrazino, 1-ethylhydrazino, 2-ethylhydrazino, 1,2-dimethylhydrazino, 2,2-dimethylhydrazino, 1,2,2-trimethylhydrazino and 2-phenylhydrazino; azido; sulfo, alkoxy sulfonyl or aryloxysulfonyl of up to 7 carbon atoms, such as, for example, methoxysulfonyl, ethoxysulfonyl, or p-tolyloxysulfonyl; sulfur (as the thione group) and/or oxygen, preferably as the keto or N-oxido group (N-oxide).

If secondary amino groups are present in the R-group, these can be substituted by various acyl groups, for example, by an optionally unsaturated aliphatic acyl group of 1–18 carbon atoms, e.g., formyl, acetyl, propionyl, butyryl, isobutyryl, pentanoyl, hexanoyl, heptanoyl, octanoyl, nonanoyl, decanoyl, dodecanoyl, palmitoyl, stearoyl, oleoyl, linoloyl, linolenoyl; or by an alkoxyacetyl group of 1–4 carbon atoms in the alkoxy group, e.g., methoxyacetyl, ethoxyacetyl, propoxyacetyl, butoxyacetyl, isobutoxyacetyl, tert.-butoxyacetyl; or by a mono- or disaccharide group oxidized to the carboxylic acid on the number 1 carbon atom and/or on the terminal-positioned carbon atom, e.g., gluconoyl, glucuronoyl, saccharoyl, galactonoyl, galacturonoyl, mucoyl, mannonoyl, mannosaccharoyl, arabinonoyl, ribonoyl, maltobionoyl, lactobionoyl, saccharobionoyl; or by the acyl group of a dicarboxylic acid (of 4–8 carbon atoms) which can form cyclic anhydrides, e.g., 3-carboxypropionyl (succinoyl), 3-carboxy-cis-prop-2-enoyl (maleinoyl), 2-carboxycyclohexylcarbonyl, phthaloyl, 2- or 3-carboxypyridyl-3- or -2-carbonyl, 3-(carboxyethylmercapto)-propionyl; or by a sulfone group.

If carboxy or sulfo groups are present in the R group, these can also be present in the form of their alkali metal, alkaline earth metal or ammonium salts, preferably in the form of their sodium or potassium salts.

The starting materials of Formula 2 can be utilized in the form of the free acids or as functional derivatives thereof. Suitable functional derivatives are, for example, alkyl esters, lactones, halogenides, azides, as well as anhydrides. The alkyl groups of the esters can contain up to 4 carbon atoms and can be, for example, methyl, ethyl, propyl, isopropyl, n-butyl, isobutyl, and tert.-butyl. Suitable lactones are, e.g., 4-butyrolactone, as well as 4- and 5-valerolactone, as well as 3-hydroxy-3-methyl-5-valerolactone. Preferred halogenides are the chlorides or bromides, as well as the fluorides or iodides. Suitable anhydrides are, in addition to the symmetrical anhydrides, also mixed, cyclic, and Leuchs anhydrides, insofar as these can be formed. Preferred acyloxy groups in the mixed anhydrides (compounds 2 wherein the OH-group is substituted by acyloxy) are the trifluoroacetoxy, acetoxy and formyloxy groups, as well as propionyloxy, butyryloxy, isobutyryloxy. Cyclic anhydrides can be derived from dicarboxylic acids, for example, from glutaric acid, maleic acid, succinic acid, cyclobutane-1,2-dicarboxylic acid, cyclopentane-1,2-dicarboxylic acid, cyclohexane-1,2-dicarboxylic acid, phthalic acid. Leuchs anhydrides are formed, for example, from amino acids and phosgene, e.g., from the 1-amino-1-carboxylic acids of cyclobutane, cyclopentane, cyclohexane, cycloheptane, cyclooctane or thiopyran, as well as from aliphatic amino acids, such as glycine, leucine and isoleucine.

Of the groups wherein X is arylsulfonyloxy, preferred are phenylsulfonyloxy and p-tolylsulfonyloxy, as well as, for example, naphthyl-1-sulfonyloxy or naphthyl-2-sulfonyloxy.

The preparation of the compounds of Formula 1 and also the conversion of thus-produced compounds of Formula 1 into other compounds of Formula 1 takes place otherwise in accordance with methods known from the literature (described, for example, in the standard works such as Houben-Weyl, "Methoden der Organischen Chemis," [Methods of Organic Chemistry], Georg-Thieme publishers, Stuttgart), namely under the reaction conditions known and suitable for the individual reactions.

All starting materials for the preparation of the compounds of Formula 1 can, if desired, also be formed in situ so that they are not isolated from the reaction mixture but rather are immediately further reacted to compounds 1.

The compounds 1 can preferably be produced by reacting HPI with a carboxylic acid 2 or one of the functional derivatives thereof. Preferred functional derivatives are the carboxylic acid anhydrides, also mixed carboxylic acid anhydrides, e.g., the p-fluorobenzoic acid-formic acid anhydride, the carboxylic acid halogenides (e.g., the fluoride, chloride, bromide, iodide), or the azides. An excess of the carboxylic acid derivative can be used as the solvent, or an inert solvent is used, for example, aromatic hydrocarbons, such as benzene or toluene; ethers, such as diisopropyl ether, tetrahydrofuran (THF), or dioxane; nitriles, such as acetonitrile; or halogenated hydrocarbons, such as dichloromethane, chloroform, carbon tetrachloride, or chlorobenzene. During the acylation, an inorganic or organic base is preferably added, e.g., sodium hydroxide, potassium hydroxide, sodium or potassium carbonate, pyridine, triethylamine, triisopropylamine. The reaction with the acid 2 itself is conducted between about 0° and 200°; when using the functional derivatives of the acid, the reaction is carried out between about 0° and the boiling point of the solvent used, preferably between about 0° and 80°. The reaction times range between about 10 minutes and 48 hours, preferably between 30 minutes and 5 hours.

It is also possible to produce the carboxylic acid halogenides, especially the chlorides, in situ, for example from the carboxylic acids of Formula 2 and halogenating reagents, e.g., silicon tetrachloride, phosphorus trichloride or -bromide phosphorus oxychloride, thionyl chloride, or phosphorus pentachloride, suitably in one of the aforementioned solvents and/or with the addition of one of the above-mentioned organic bases. Temperatures of 40°-200°, especially 70°-140°, are preferred.

The reaction of HPI with a free carboxylic acid 2 can be accomplished, for example, in the presence of dicyclohexylcarbodiimide in one of the aforementioned inert solvents or in pyridine. Low temperatures (e.g., 0°-20°) are preferred for this reaction.

It is also possible to react the HPI with one of the above-mentioned lactones, suitably in the presence or absence of a basic catalyst, such as sodium or potassium hydride, usually in the presence of an inert solvent, such as xylene, dimethylformamide (DMF), dimethyl sulfoxide, sulfolane, dioxane, THF, or diethyl ether at temperatures of between about 0° and about 200°.

In addition to the racemic HPI, one of its two optical antipodes can also serve as the starting material. Preferably, the (−)-antipode is used, which can be converted, by acylation, into pharmacologically particularly valuable, optically active compounds 1.

The starting compounds (HPI as well as the carboxylic acids of Formula 2) are known or can be prepared analogously to conventional compounds according to standard methods.

It is also possible to obtain compounds of Formula 1 by cyclizing a compound of Formula 3 in the presence of a cyclizing agent under conditions wherein HX is split off. Suitable cyclizing media are strong bases, such as preferably butyllithium or potassium tert.-butylate, further phenyllithium, sodium hydride, alcoholates such as sodium or potassium methylate, ethylate, propylate, isopropylate, n-butylate, tert.-butylate, amides such as lithium diisopropylamide or the corresponding sodium or potassium amide. Normally, the reaction is carried out in inert solvents, such as benzene, hexane, tert.-butanol, THF, hexamethylphophoric triamide, dioxane, ether, DMF, dimethyl sulfoxide, acetonitrile, optionally under nitrogen. The reaction temperatures range between about −20° and the boiling point of the solvent used. The reaction takes between about 15 minutes and about 30 hours, preferably 10-14 hours.

The cyclization can also be effected with optically active compounds of Formula 3, which leads to optically active compounds 1.

The starting compounds of Formula 3 are accessible according to methods known from the literature, for example from the corresponding 1-cyano-1,2-dihydro- or 1-cyano-1,2,3,4-tetrahydroisoquinolines substituted in the 2-position by the residue R—CO— (having the values given for Formula 1). These compounds are hydrogenated on Raney nickel at elevated temperatures and pressures, the R—CO group migrating, to the corresponding N-(1,2,3,4-tetrahydroisoquinolyl-1-methyl)-acylamides which can then be converted, with compounds of the formula X—CH$_2$—CO—X, e.g., chloracetyl chloride, into the compounds 3.

It is furthermore possible to produce the compounds of Formula 1 by the reduction, preferably the catalytic hydrogenation, of a compound of Formula 4. Suitable catalysts are those known from the literature in this connection, preferably noble metal catalysts, but also copper-chromium oxide, as well as nickel and cobalt catalysts. The noble metal catalysts can be used, for example, as supported catalysts (e.g., palladium on charcoal), as oxide catalysts (e.g., platinum oxide), or as finely divided metallic catalysts (e.g., platinum black). Nickel and cobalt catalysts are suitably employed as the Raney metals, and nickel is utilized also on kieselguhr or pumice as the support. The hydrogenation can be conducted under pressures of between about 1 and 200 atmospheres and temperatures of between about 0° and 200°, advantageously in the presence of a solvent, preferably an alcohol, such as methanol, ethanol, isopropanol, or tert.-butanol; ethyl acetate, an ether such as dioxane or THF; water; and/or an alkaline solution. If desired, the hydrogenation can also be effected in a homogeneous phase. Suitable catalysts for this purpose are, for example, complex compounds of heavy metals, e.g., soluble rhodium complexes, such as rhodium hydridocarbonyl-tris(triphenylphosphine).

The reduction of compounds 4 can also be controlled so that solely one antipode of compounds 1 is produced, or is obtained to a predominant extent. This can be done, for example, by asymmetrical hydrogenation. A suitable catalyst for this reaction is Raney nickel, for example, which had previously been treated with asymmetrically modifying reagents, e.g., with aqueous solutions of optically active hydroxy or amino acids, such as tartaric acid, citric acid, alanine, isoleucine, lysine, phenylalnine, valine, or leucine.

Furthermore, heavy metal catalysts applied to natural or synthetic polymers can be utilized for an asymmetrical hydrogenation, for example palladium or platinum on silk or on specially prepared silica gel or polyamino acid supports as described in the literature. In the homogeneous phase, an asymmetrical hydrogenation is accomplished, for example, on optically active soluble rhodium complexes. The asymmetrical hydrogenation is effected under the above-indicated conditions, preferably at 1–3 atmospheres and temperatures of between 20° and 50°.

The starting compounds 4 can be prepared, for example, by dehydrogenating a corresponding compound of Formula 1, saturated in the 11b(1)-position, with sulfur, selenium, chloranil, or another dehydrogenating agent known from the literature. Such a reaction is of interest, in particular, if the compound saturated in the 11b(1)-position is present as an optically active antipode and is less effective than the other possible antipode. In this case, the lesser effective antipode can be converted, by dehydrogenation, into compound 4, and the latter can be converted, by subsequent hydrogenation, into the more effective saturated racemate of Formula 1 or, by asymmetrical hydrogenation, primarily into the more effective antipode of Formula 1.

In a thus-obtained compound of Formula 1, the R group can optionally be converted into another R group according to methods disclosed in the literature. For example, already present substituents can be converted into other substituents.

Thus, it is possible to reduce a reducible substituent, such as the nitro group, suitably by catalytic hydrogenation or also by chemical methods. The catalytic hydrogenation can be conducted according to the above-mentioned conditions. Suitable for reducing purposes are also metals (e.g., iron, zinc) with acids (e.g., HCl, $CH_3COOH$) or tin (II) chloride.

An additional keto group in the acyl residue of compound 1 can be converted into a hydroxy group by hydrogenation or by chemical reaction. The above-mentioned methods are preferred for conducting the hydrogenation. Furthermore, the keto group can be reduced with nascent hydrogen, e.g., by treatment with zinc/acid or zinc/alkaline solution; a suitable acid, for example, is acetic acid. Also sodium or another alkali metal can be used in a lower alcohol (such as ethanol, isopropanol, isoamyl alcohol). The keto group can also be reduced with metallic hydrides. Preferred are complex metallic hydrides which do not attack the amide group of the ring system, such as sodium borohydride, lithium borohydride, potassium tri-(sec.-butyl)-borohydride, potassium trimethoxyborohydride, suitably in the presence of an inert solvent, such as an ether, e.g., diethyl ether, THF, dioxane, 1,2-dimethoxyethane, or diglyme. Sodium borohydride can also be used in an aqueous or aqueous-alcoholic solution. The reaction takes place between about −80° and +100°, especially between −20° and the boiling point of the solvent utilized.

Furthermore, a keto group can be converted into a methylene group by reaction with hydrazine and subsequent decomposition of the thus-formed hydrazone according to the method by Wolff-Kishner. Also, it is possible according to the above-mentioned conditions to hydrogenate double bonds to single bonds and triple bonds to double or single bonds. With the aid of hydrogen/palladium, it is also possible to reduce an N-oxide group in the R group to the corresponding tertiary amine in accordance with known methods.

A thus-obtained compound 1 which contains a tertiary nitrogen atom in the acyl residue can be converted into the corresponding N-oxide by reaction with inorganic or organic peroxides, e.g., hydrogen peroxide (preferably a 30% aqueous solution or mixtures of hydrogen peroxide with formic acid), peracetic acid, perbenzoic acid, 3-chloroperbenzoic acid, or tert.-butylhydroperoxide. Suitable solvents for the organic peroxides are, for example, methylene chloride, chloroform, or alcohols such as methanol or isopropanol. The reaction is conducted at temperatures of between about 0° and 50°, preferably at room temperature. The reaction times range between about 1 and 48 hours.

Thus-obtained compounds 1 carrying a mercapto group in the R group can be oxidized to the corresponding sulfo compounds for example with nitric acid. Analogously, corresponding alkylmercapto compounds can be converted into sulfoxides or sulfones, for example with nitric acid, aqueous solutions of hydrogen peroxide, or 3-chloroperbenzoic acid.

Alcohol groups in the R group can be converted into carbonyl groups, for example by oxidation with manganese dioxide or chromic acid.

Compounds 1 containing one or more free hydroxy, mercapto, amino, or monoalkylamino groups as substituents can be alkylated to the corresponding alkoxy, alkylmercapto, monoalkylamino, dialkylamino, or trialkylammonium compounds, or they can be acylated to the corresponding acyl compounds.

For the O- and S-alkylation, the starting compounds are suitably first converted into the corresponding salts by the addition of a base, e.g., sodium hydroxide solution, potassium hydroxide, or potassium carbonate. Suitable alkylating agents are, for example, alkyl halogenides, such as methyl chloride, bromide, or iodide, ethyl chloride, bromide, or iodide, the corresponding dialkylsulfuric acid esters or the alkylsulfonic acid esters, e.g., dimethyl sulfate, diethyl sulfate, or methyl p-toluenesulfonate, or diazo compounds, such as diazomethane. Amino compounds can also be reductively alkylated with formaldehyde or acetaldehyde in the presence of hydrogen on a catalyst or in the presence of formic acid. Suitable solvents are, for example, water; aqueous sodium hydroxide solution; alcohols, such as methanol, ethanol, or n-butanol; hydrocarbons, such as benzene or xylene; ethers, such as THF or dioxane; amides, such as DMF. The alkylations take place suitably at temperatures between about −10° and about +150°, especially between room temperature and boiling temperature of the solvent employed.

A corresponding acylation takes place suitably with carboxylic acids or carboxylic acid derivatives, for example under the conditions indicated above for the acylation of HPI. An acylation can also be accomplished with ketenes, preferably in inert solvents, such as ether, dichloromethane, chloroform, benzene, or toluene, optionally with the addition of acidic catalysts, such as sulfuric acid or p-toluenesulfonic acid. Thus, it is possible, for example, to obtain from 2-(4-hydroxybenzoyl)-HPI and ketene the final product 2-(4-acetoxybenzoyl)-HPI.

By reacting thus-obtained compounds of Formula 1 which contain a primary or secondary amino group in the R group with a derivative of a saccharic acid under the above-mentioned conditions, compounds can be prepared wherein the amino group in the R group is masked by a saccharic acid group. Suitable saccharic acid R groups are, for example, the lactones of the sugars, such as gluconic acid lactone or glucuronic acid lactone.

It is also possible to react amino groups in the R group with a saccharic acid (or a functional derivative thereof) masked on the remaining OH-groups (for example by benzyl groups), and then split off the masking groups (for example by hydrogenation). Thus, 2-(4-gluconoylaminobenzoyl)-HPI can be produced, for example, by reaction of 2-(4-aminobenzoyl)-HPI with 2,3,4,5,6-penta-O-benzyl-gluconoyl chloride and subsequent hydrogenolysis of the benzyl groups in the thus-obtained 2-[4-(2,3,4,5,6-penta-O-benzyl-gluconoylamino)-benzoyl]-HPI.

Compounds 1, the amino group or groups of which is (are) masked in the R group by one (or several) sulfo group(s), can be obtained from thus-produced compounds 1 with one (or several) free amino group(s) in the R group by reaction with chlorosulfonic acid, for example under the conditions disclosed above for the reaction of HPI with acid halogenides.

It is also possible to convert acyloxy (e.g., formyloxy, acetoxy, trifluoroacetoxy, phthaloyloxy, or other readily saponifiable acyloxy groups), acylmercapto, or alkoxycarbonyl (e.g., methoxycarbonyl or ethoxycarbonyl) groups in thus-obtained compounds of Formula 1 by treatment with solvolyzing agents into hydroxy, mercapto, or carboxy groups. For this purpose, acids are utilized (such as hydrochloric acid or acetic acid), or preferably bases are employed, such as sodium or potassium carbonate, calcium, barium, sodium, or potassium hydroxide, for example in aqueous methanol. Gentle reaction conditions are preferred so that the acid amide groups are not attacked. In general, the reaction is accomplished at temperatures of between about $-40°$ and $+90°$ and in a period of 2-50 hours.

Cyano groups in compounds 1 can be hydrolyzed to carbamoyl groups in an acidic medium (e.g., with HCl or $H_2SO_4$ in water, methanol, ethanol, aqueous dioxane, or acetic acid) or in an alkaline medium (e.g., with KOH in aqueous ethanol or in cyclohexanol). It is also possible to conduct the reaction with $H_2O_2$ in an alkaline solution, generally at temperatures of between room temperature and 80° during a period of 1-5 hours.

Compounds 1 wherein an amino group in the acyl group is masked in the form of a Schiff base can be converted into the corresponding secondary amines by hydrogenolysis. The Schiff bases are preferably derived from aldehydes, such as formaldehyde, benzaldehyde, or glyoxylic acid, and also from ketones, such as acetone. For the hydrogenation, hydrogen is used, for example, in the presence of platinum or Raney nickel at room temperature and under normal pressure.

Benzylamino compounds can be split into the corresponding primary amines, for example, with hydrogen in the presence of a noble metal catalyst, such as palladium.

It is also possible to convert thus-produced Schiff bases by reaction with bisulfite into the corresponding bisulfite adducts. The bisulfite adducts can also be obtained by the direct reaction of an aldehyde-bisulfite addition product with a compound 1 which carries a free amino group in the R group.

Urethane groups, e.g., N-ethoxycarbonyl or N-benzyloxycarbonyl groups, in the R group of compounds 1 can be split, for example with hydrogen chloride in acetic acid.

From thiourethane groups present in the R group of compounds 1, the corresponding amino groups can be liberated with alkali metal acetate or lead (II) acetate in alcohols, such as methanol or ethanol, or with alkali metal hydroxide solution in the presence of lead (II) hydroxide or lead (II) carbonate.

Quite basically, suitable masking groups for an amino group in the acyl residue of compounds 1 are all those successfully employed in peptide syntheses. Correspondingly, methods known from the literature can also be used to split off these masking groups.

It is further possible to convert an alkylamino substituent in compounds 1 into a 1-alkylhydrazino substituent, for example by reaction with nitrous acid and reduction of the thus-produced nitrosamine with nascent hydrogen (e.g., from zinc/acetic acid) or with tin(II) chloride.

Furthermore, keto groups in the R group of compounds 1 can be converted into amino groups. For example, the ketones can be reacted with hydroxylamine or with hydrazine, and the thus-produced oximes or hydrazones can be hydrogenated, for example, on Raney nickel at about 1-50 atmospheres. According to another mode of operation, ketones can be hydrogenated in the presence of ammonia or primary or secondary amines. In this case, primary, secondary, or tertiary amines 1 are obtained. The reaction proceeds preferably under pressures of between 1 and 200 atmospheres and at temperatures of between $-40°$ and $150°$ in methanol, ethanol, isopropanol, THF, dioxane, or liquid ammonia, for example.

Furthermore, keto groups in compounds 1 can be converted according to customary methods into $CF_2$-groups, for example with sulfur tetrafluoride or phenylsulfur trifluoride in the presence of hydrofluoric acid or also with carbonyl difluoride in the presence of pyridine. The reaction is preferably conducted in an autoclave under slight excess pressure in inert solvents, such as methylene chloride, chloroform, or THF at temperatures of between 0° and 150°.

It is also possible to split alkoxy or alkylmercapto groups present in thus-obtained compounds 1, thus producing hydroxy or mercapto groups. In this reaction, conditions must be selected under which the acid amide groupings remain preserved. Suitably, a Lewis acid is utilized, such as boron tribromide, in an inert solvent, such as dichloromethane, chloroform, or carbon tetrachloride at temperatures of between about $-40°$ and $+50°$.

Compounds 1 containing one or more amino groups can be converted into the corresponding diazonium compounds in accordance with conventional methods by diazotization; in these diazonium compounds, the diazonium group can be exchanged, for example, against fluorine, chlorine, bromine, iodine, cyano, OH, SH, O-alkyl, or S-alkyl. The diazotization of the corresponding amino compounds can be effected, for example, in a sulfuric acid, hydrochloric acid, hydrobromic acid and/or tetrafluoboric acid aqueous solution by adding an inorganic nitrite, preferably $NaNO_2$ or $KNO_2$, at temperatures of between about $-20°$ and $+10°$. It is also possible to conduct the reaction with an organic nitrite, such as n-butyl nitrite, n-amyl nitrite, or isoamyl nitrite, at temperatures of between $-20°$ and $+5°$ in inert organic solvents, such as diethyl ether, THF, or dioxane.

To introduce a fluorine atom, the diazotization is conducted, for example, in anhydrous hydrofluoric acid, thereafter heating the reaction mixture; alternatively, the diazonium salts are reacted with $HBF_4$ to the sparingly soluble diazonium tetrafluoborates. The latter can be isolated and converted by a heat treatment, e.g., by heating in an inert solvent, to the desired fluorine compounds. The diazonium tetrafluoborates (especially those of heterocyclic compounds) can, however, also be irradiated, without isolation, in an aqueous suspension with a mercury lamp, thus yielding the desired fluorine compounds. The diazonium group can be exchanged against chlorine or bromine preferably in a hot aqueous solution in the presence of $Cu_2Cl_2$ or $Cu_2Br_2$. The exchange of a diazonium iodide group against iodine is accomplished already by slight heating, and in this reaction $Cu_2I_2$, $Cu_2Br_2$, or $Cu_2Cl_2$ can be added to the mixture. A replacement of the diazonium group by CN is accomplished, for example, in the presence of $Cu_2(CN)_2$ and alkali metal cyanides (such as NaCN, KCN) at about $0°$ to $+5°$. The diazonium salt grouping can also be exchanged against an alkoxy group, for example by heating in an aqueous-alcoholic solution. An exchange against a mercapto group takes place suitably by reacting the diazonium compound with an alkali metal xanthate, e.g. with sodium ethyl xanthate, and subsequent alkaline saponification.

The diazonium compounds can also be coupled, with the use of suitable couplers, to the corresponding azo dyes. Primarily feasible couplers are benzene derivatives carrying activating substituents, such as amino, alkylamino, dialkylamino, hydroxy, or alkoxy groups and which can furthermore contain additional substituents, such as carboxy, halogen (preferably fluorine or chlorine), sulfo, or alkyl groups.

Basic compounds 1 can optionally be converted into the physiologically acceptable acid addition salts thereof. Suitable for this purpose are inorganic or organic, e.g. aliphatic, alicyclic, araliphatic, aromatic, or heterocyclic mono- or polybasic carboxylic or sulfonic acids, e.g. mineral acids, such as hydrochloric, hydrobromic, or hydriodic acid, sulfuric acid, nitric acid, phosphoric acids, such as orthophosphoric acid, sulfamic acid; organic acids, such as formic, acetic, propionic, butyric, pivalic, diethylacetic, oxalic, malonic, succinic, pimelic, fumaric, maleic, citric, gluconic, lactic, tartaric, malic, benzoic, salicylic, phenylpropionic, ascorbic, isonicotinic, methanesulfonic, ethanedisulfonic, 2-hydroxyethanesulfonic (isethionic), p-toluenesulfonic, naphthalene- mono- or -disulfonic acids (for example naphthalene-1- or -2-sulfonic or naphthalene-1,5- or -2,6-disulfonic acid).

Compounds 1 with a free carboxyl or sulfo group can be converted into one of their physiologically acceptable metal or ammonium salts by reaction with a base. Especially suitable salts are the sodium, potassium, magnesium, calcium, and ammonium salts, furthermore substituted ammonium salts, such as, for example, the dimethyl- and diethylammonium, cyclohexylammonium, dicyclohexylammonium, N-alkyl- or N-aryl-substituted piperazinium salts (such as the methylpiperazinium or ethylpiperazinium salts), as well as the N,N-dibenzylethylenediammonium salts.

Conversely, basic compounds 1 can be liberated from the acid addition salts thereof by treatment with bases, such as sodium or potassium hydroxide, sodium or potassium carbonate, and acidic compounds 1 can be liberated from their metallic and ammonium salts by treatment with acids, especially mineral acids, such as dilute hydrochloric or sulfuric acid.

Compounds 1 carrying a primary, secondary, or tertiary amino group can be converted into the physiologically acceptable quaternary ammonium salts thereof by treatment with quaternizing alkylating agents, such as methyl iodide, dimethyl sulfate, or ethyl halogenides.

Optically active compounds of Formula 1 are suitably obtained by the use of starting materials which are already optically active. Preferably, the antipodes of HPI or those of compound 3 are used as starting compounds. However, it is likewise possible to split thus-produced racemates of Formula 1 into the optical antipodes thereof. The method of chemical separation is preferred. Thus, a racemate of Formula 1 can, for example, be reacted with an optically active auxiliary agent, and the thus-obtained diastereomeric mixtures can be split in a suitable manner. For example, a racemate of Formula 1 carrying an acidic group (e.g., a carboxyl group) can be reacted with an optically active base or, conversely, a racemate 1 carrying a basic group (e.g., an amino group) can be reacted with an optically active acid. Suitable as optically active bases are for example amines, such as quinine, cinchonidine, brucine, cinchonine, hydroxyhydrindamine, morphine, 1-phenylethylamine, 1-naphthylethylamine, quinidine, strychnine, basic amino acids (such as lysine or arginine), or amino acid esters. Conversely, suitable as optically active acids are the (+)- and (−)-forms of tartaric acid, dibenzoyltartaric acid, diacetyltartaric acid, camphoric acid, β-camphorsulfonic acid, mandelic acid, malic acid, 2-phenylbutyric acid, dinitrodiphenic acid, lactic acid, or quinic acid. The thus-obtained diastereomeric mixtures can subsequently be separated by selective crystallization or by manual screening. The isolated diastereomeric compounds can finally be separated hydrolytically into the desired optically active compounds of Formula 1.

The compounds 1 are effective preferably against cestodes and trematodes. They can optionally be used against the following cestodes (arranged according to hosts):

1. Ruminants: Moniezia, Stilesia, Avitellina, Thysanosoma, Thysaniezia, cysticerci of Taenia sp., *Coenurus cerebralis, Echinococci cysticerci.* 2. Equine animals: Anoplocephala. 3. Rodents: Hymenolepis (especially *H. nana* and *H. diminuta*). 4. Fowl: Davainea, Raillietina, Hymenolepis. 5. Canine and feline animals: Taenia (especially *T. hydatigena, T. pisiformis, T. taeniaeformis, T. ovis, T. serialis, T. cervi, T. multiceps*), Dipylidium (especially *D. caninum*), Echinococcus (particularly *E. granulosus* and *E. multilocularis*). 6. Man: Taenia (in particular *T. solium, T. saginata, T. serialis*), Hymenolepis (especially *H. nana* and *H. diminuta*), Drepanidotaenia, Dipylidium, Diplopylidium, Coenurus (especially *C. cerebralis*), Diphyllobothrium (particularly *D. latum*), *Echinococcus cysticerci* (especially those of *E. granulosus* and *E. multilocularis*). Among the trematodes of significance from the viewpoints of human and veterinary medicine are primarily those of the family of the Schistosomidae, especially the genus Schistosoma (*Sch. mansoni, Sch. haematobium, Sch. japonicum*) which must be combated. Optionally, the genera Fasciola, Dicrocoelium, Clonorchis, Opisthorchis, Paragonimus, Paramphistomum, Echinostoma, and others can likewise be targets of attack.

The compound 1 can be utilized, inter alia, in the following host and/or intermediate host organisms for the combating of cestodes and/or trematodes and/or the larvae thereof: Man, types of monkeys, the most important domestic and wild animals, e.g., Canidae, such as dogs, foxes; Felidae, such as cats; Equidae, such as horses, donkeys, mules; Cervidae, such as roe deer, red deer, fallow deer; chamois; rodents; ruminants, such as cattle, sheep, goats; birds, such as chickens, ducks; pigs; fish.

As the biotope of the affectable parasites or the larvae thereof, worth mentioning are especially the gastrointestinal tract, e.g., stomach, intestine, pancreas and/or bile duct. However, other organs can also be affected (e.g., liver, kidney, lungs, heart, spleen, lymph nodes, brain, spinal marrow, or testes), abdominal cavity, connective tissue, musculature, peritoneum, pleura, or diaphragm, lungs and/or blood vessels; thus, the compounds 1, with good compatibility, are effective for example against Schistosoma sp. in the vascular system, against *Hymenolepis microstoma* in the bile duct, and *T. hydatigena cysticerci* in the liver.

The compounds 1 can be utilized as such as in combination with pharmaceutically acceptable inert vehicles. Such vehicles can consist, for example, of capsules, solid diluents or fillers, sterile aqueous media and/or various nontoxic organic solvents.

Suitable forms of administration are, inter alia, tablets and dragees (optionally containing the effective agent in a timed-release form), effervescent tablets, capsules, granules, aqueous suspensions, injectable solutions, emulsions and suspensions, elixirs, syrups or pastes. The formulations for this purpose are produced conventionally, for example by adding the active agents to solvents and/or carrier substances optionally with the use of emulsifiers and/or dispersing agents. Auxiliary substances in this connection are, for instance: water, nontoxic organic solvents (e.g., paraffins or alcohols, such as glycerin or polyethylene glycol), vegetable oils (e.g., sesame oil), solid carriers, such as natural or synthetic rock flours (e.g., talc or highly disperse silicic acid), sugar, emulsifiers (e.g., ionic or nonionic compounds), dispersing agents (e.g., methylcellulose and polyvinylpyrrolidone) and/or lubricants (e.g., magnesium stearate). Tablets can also contain additives, such as sweeteners, sodium citrate, calcium carbonate and dicalcium phosphate, together with further substances such as amylose, gelatin, etc. Aqueous suspensions and/or elixirs can optionally be combined with flavor-ameliorating agents or coloring substances. The compounds 1 can optionally also be administered without, or almost without, auxiliary substances, for example in capsules.

The effective agents 1 are preferably administered orally, but it is also possible to effect a parenteral, especially subcutaneous or intramuscular, as well as a dermal administration.

To combat adult cestodes, it is advantageous to administer the effective agents once or several times in daily amounts of 0.01-250 mg./kg., preferably about 0.5-100 mg./kg. orally or subcutaneously. When combating the corresponding tapework larvae (cystercerci) and/or when combating the Schistosoma, larger amounts of active agent may be necessary.

When giving larger amounts of effective agent, it is also possible to distribute smaller dosages over the day. Thus, instead of 1000 mg. in a single dose, one can administer 5 separate doses of respectively 200 mg. In the veterinary medicine, it is also possible to give the effective agents together with the feed; suitably, premixes to be added to the feed are produced. Here again, all customary additives can be utilized.

In certain cases, the aforementioned amounts must be changed, namely in dependence on the body weight and the type of application, but also on the basis of the species and its individual behavior with respect to the medicinal agent and/or the type of its formulation and/or the instant and/or interval at which the agent is administered. Thus, it may be sufficient in some cases to make do with less than the aforementioned minimum amount, while in other instances the above-mentioned upper limit must be exceeded.

Depending on the type of application, the ratio between the compounds 1 and the carrier and/or auxiliary agent employed can vary greatly. If a compound 1 is administered, for example, as a tablet or dragee, it is possible to combine about 0.01-2500 mg. of active agent with about 1-10,000 mg. of auxiliary agent. In contrast thereto, if a compound 1 is formulated as a premix for a medical feed, about 0.1-400 g. of compound 1 can be used per about 1 kg. of carrier or auxiliary agent. When formulated in an injection fluid, a solution of 1 l. of liquid can contain, depending on the type of solubilizer, about 0.5-100 g. of a compound 1; similarly, 1 l. of fluid can contain about 0.5-250 g. of a compound 1 dissolved and/or suspended therein.

The compounds 1 can be present in the formulations also in mixtures with other effective agents. Thus, it is useful to attain a broader spectrum of effectiveness optionally to add an effective agent active on nematodes, e.g., thiabendazole [2-(4-thiazolyl)benzimidazole] or piperazine (or piperazine derivatives, such as N-methylpiperazine). It is also possible to administer two or more compounds of general Formula 1 in combination.

The anthelmintic effect of the substances will be explained in greater detail with reference to the following examples of their application:

A. PHARMACOLOGICAL EXAMPLES

The following compounds were tested in these examples:

Effective Agent
 A. 2-(4-aminobenzoyl)-HPI
 B. 2-(3-fluorobenzoyl)-HPI
 C. 2-cyclohexylcarbonyl-HPI
 D. 2-(4-tetrahydropyranylcarbonyl)-HPI E. 2-(3-thienylcarbonyl)-HPI
 F. 2-(4-nitrobenzoyl)-HPI
 G. 2-nicotinoyl-HPI
 H. 2-isobutyryl-HPI The following products were used for comparison:

Quinacrine [2-methoxy-6-chloro-9-[(1-methyl-4-diethylaminobutyl)-amino]-acridine], Niclosamide [N-(2-chloro-4-nitrophenyl)-5-chlorosalicylamide], Dichlorophen (2,2'-dihydroxy-5,5'-dichlorodiphenylmethane), Lucanthone [1-(2-diethylaminoethylamino)-4-methylthioxanthone hydrochloride], Niridazole [1-(5-nitro-2-thiazolyl)-imidazolidin-2-one], and Stibophen [sodium antimony bis(pyrocatechol-2,4-disulfonate)].

EXAMPLE (a)

*Hymenolepis nana*, adults, larvae/mice

*Hymenolepis microstoma*, adults/mice

*Hymenolepis diminuta*/rats

Test animals experimentally infected with *H. nana*, *H. microstoma*, or *H. diminuta* are treated 1-3 days after infection (larvae) and/or after the prepatent period of the parasites has elapsed. The quantity of active agent is applied as an aqueous suspension orally and subcutaneously, respectively.

The degree of effectiveness of the preparation is determined by counting, after dissection, the worms which remained in the test animal, as compared to untreated control animals, and thus calculating the effectiveness, in percent.

TABLE 1

| | (Example [a]) | |
|---|---|---|
| Effective Agent | Parasite | Effective Minimum Dosage in mg./kg. (Parasite Reduction > 90%) |
| A | H. nana - adults | 20 |
| | H. nana - larvae | 100 |
| | H. microstoma | 50 |
| | H. diminuta | 25 |
| B | H. nana - adults | 50 |
| | H. diminuta | 100 |
| C | H. nana - adults | 20 |
| | H. microstoma | 100 |
| | H. diminuta | 25 |
| D | H. nana - adults | 50 |
| | H. diminuta | 50 |
| E | H. nana - adults | 250 |
| | H. diminuta | 250 |
| F | H. nana - adults | 50 |
| | H. diminuta | 50 |
| G | H. nana - adults | 20 |
| H | H. nana - adults | 50 |
| Quinacrine | H. diminuta | >1000 |
| Niclosamide | H. nana - adults | 500 |
| | H. nana - larvae | ineffective |
| | H. microstoma | 500 |
| Dichlorophen | H. nana - adults | >1000 |
| | H. diminuta | 500 |

EXAMPLE (b)

*Taenia taeniaeformis*, larvae (cysticerci)/mice

Mice infected experimentally with *Taenia taeniaeformis* larvae are treated about 2-5 months after infection. The amount of active agent is applied orally as an aqueous suspension.

The degree of activity of the preparation is determined by counting, after dissection, the number of living and killed-off larvae as compared to untreated control animals, and then calculating the percentage of effectiveness.

TABLE 2

| | (Example [b]) |
|---|---|
| Effective Agent | Effective Minimum Dosage in mg./kg. (Parasite Reduction > 90%) |
| A | 100 |
| Quinacrine | ineffective |
| Niclosamide | ineffective |

EXAMPLE (c)

*Taenia* spec./dogs

Dogs infected experimentally or naturally with *Taenia hydatigena* or *Taenia pisiformis* are treated after the prepatent period of the parasites has elapsed.

The amount of active agent is administered orally as pure effective compound in gelatin capsules.

TABLE 3

| | (Example [c]) |
|---|---|
| Effective Agent | Effective Minimum Dosage in mg./kg. (Parasite Reduction > 90%) |
| A | 10 |
| B | 25 |
| C | 10 |
| D | 10 |
| E | 10 |
| H | 10 |
| Niclosamide | 50 |

The degree of effectiveness is determined by counting the worms excreted after the treatment and the worms remaining in the test animal after dissection, and then calculating the percentage of the excreted worms.

EXAMPLE (d)

*Echinococcus multilocularis*/dogs

Dogs infected experimentally with *Echinococcus multilocularis* are treated between the 25th and 29th day after infection.

The amount of active agent is administered as the pure effective compound orally in gelatin capsules. The degree of effectiveness is calculated analogously to Example (a).

TABLE 4

| | (Example [d]) |
|---|---|
| Effective Agent | Effective Minimum Dosage in mg./kg. (Parasite Reduction > 90%) |
| A | 50 |
| B | 50 |
| C | 50 |
| Niclosamide | effectiveness unsatisfactory to total lack in effectiveness |

EXAMPLE (e)

*Schistosoma mansoni*/mice

Mice experimentally infected with *Schistosoma mansoni* are treated after the prepatent period of the parasites has elapsed.

The effective agent is administered orally in aqueous suspension. The effect is determined after dissection of the test animals by counting the surviving parasites and the killed-off parasites.

TABLE 5
(Example [e])

| Effective Agent | Effective Minimum Dosage in mg./kg. (Parasite Reduction > 90%) |
| --- | --- |
| A | 100 |
| B | 100 |
| C | 100 |
| D | 500 |
| H | 500 |
| Niridazole | 500 |
| Stibophen | 1000 |

In the following examples,
[α] = [α]$_D^{20}$ in chloroform;
IR = infrared spectrum in KBr.

The temperatures herein are set forth in degrees Celsius.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

At 20°, 3.71 g. of 4-nitrobenzoyl chloride in 50 ml. of chloroform is added dropwise to 4.04 g. of (±)-HPI and 2.8 ml. of triethylamine in 50 ml. of chloroform. After one hour, the reaction mixture is extracted with dilute hydrochloric acid and water. After drying and evaporation, (±)-2-(4-nitrobenzoyl)-HPI is obtained, m.p. 212°-213° (from methanol).

Analogously, the following products are prepared with the corresponding carboxylic acid chlorides:

2-acetyl-HPI, m.p. 139°
2-propionyl-HPI
2-n-butyryl-HPI
2-isobutyryl-HPI, m.p. 120°
2-n-valeryl-HPI
2-isovaleryl-HPI
2-(2-methylbutyryl)-HPI
2-trimethylacetyl-HPI, m.p. 150°
2-n-hexanoyl-HPI
2-(2-methyl-n-valeryl)-HPI
2-(3-methyl-n-valeryl)-HPI
2-(4-methylvaleryl)-HPI
2-(1-ethyl-n-butyryl)-HPI
2-(2,2-dimethyl-n-butyryl)-HPI
2-(3,3-dimethyl-n-butyryl)-HPI, m.p. 113°
2-heptanoyl-HPI, m.p. 90°-91°
2-(2,2-dimethylvaleryl)-HPI, m.p. 129°
2-octanoyl-HPI
2-(2-n-propylhexanoyl)-HPI
2-decanoyl-HPI
2-(2-n-butylhexanoyl)-HPI, m.p. 96°
2-undecanoyl-HPI
2-hexadecanoyl-HPI, m.p. 101°-102°
2-octadecanoyl-HPI
2-trifluoroacetyl-HPI
2-chloroacetyl-HPI
2-dichloroacetyl-HPI, m.p. 151°-152°
2-trichloroacetyl-HPI, m.p. 184°-185°
2-(3-chloropropionyl)-HPI
2-tris(chloromethyl)acetyl-HPI, m.p. 133°-135°
2-(2-acetoxyacetyl)-HPI
2-(2-methoxyacetyl)-HPI, m.p. 135°
2-(2-ethoxyacetyl)-HPI
2-dimethylaminoacetyl-HPI
2-diethylaminoacetyl-HPI
2-methylethylaminoacetyl-HPI
2-(2-dimethylaminopropionyl)-HPI
2-(2-diethylaminopropionyl)-HPI
2-(3-dimethylaminopropionyl)-HPI
2-(3-diethylaminopropionyl)-HPI
2-(2-dimethylamino-n-butyryl)-HPI
2-(2-diethylamino-n-butyryl)-HPI
2-(4-dimethylamino-n-butyryl)-HPI
2-(4-diethylamino-n-butyryl)-HPI
2-(2-dimethylamino-n-valeryl)-HPI
2-(2-diethylamino-n-valeryl)-HPI
2-(5-dimethylamino-n-valeryl)-HPI
2-(5-diethylamino-n-valeryl)-HPI
2-(2-dimethylamino-n-hexanoyl)-HPI
2-(2-diethylamino-n-hexanoyl)-HPI
2-(6-dimethylamino-n-hexanoyl)-HPI
2-(6-diethylamino-n-hexanoyl)-HPI
2-(2-phenylacetyl)-HPI, m.p. 123°-124°
2-(2-hydroxy-2-phenylacetyl)-HPI
2-(2-acetoxy-2-phenylacetyl)-HPI, m.p. 101°-102°
2-phenoxyacetyl-HPI
2-(4-fluorophenoxyacetyl)-HPI
2-(3-chlorophenoxyacetyl)-HPI
2-(4-chlorophenoxyacetyl)-HPI, m.p. 159°-160°
2-(3-p-fluorophenoxypropionyl)-HPI
2-(3-m-chlorophenoxypropionyl)-HPI
2-(3-p-chlorophenoxypropionyl)-HPI
2-(thienyl-2-mercaptoacetyl)-HPI, m.p. 89°-90°
2-(thienyl-3-mercaptoacetyl)-HPI
2-crotonoyl-HPI
2-methacryloyl-HPI
2-vinylacetyl-HPI
2-cinnamoyl-HPI, m.p. 152°
2-phenylpropioloyl, m.p. 155°
2-phenoxycarbonyl-HPI, m.p. 136°-137°
2-ethoxalyl-HPI, m.p. 126°
2-cyclopropylcarbonyl-HPI, m.p. 148°
2-(2-acetoxycyclopropylcarbonyl)-HPI
2-(2-fluorocyclopropylcarbonyl)-HPI
2-cyclobutylcarbonyl-HPI, m.p. 154°-155°
2-(2-ketocyclobutylcarbonyl)-HPI
2-(3-ketocyclobutylcarbonyl)-HPI
2-(2-fluorocyclobutylcarbonyl)-HPI
2-(3-fluorocyclobutylcarbonyl)-HPI
2-(2-chlorocyclobutylcarbonyl)-HPI
2-(3-chlorocyclobutylcarbonyl)-HPI
2-(2-methylcyclobutylcarbonyl)-HPI
2-(3-methylcyclobutylcarbonyl)-HPI
2-(2,2-difluorocyclobutylcarbonyl)-HPI
2-(3,3-difluorocyclobutylcarbonyl)-HPI
2-(1-acetoxycyclobutylcarbonyl)-HPI
2-(2-acetoxycyclobutylcarbonyl)-HPI
2-(3-acetoxycyclobutylcarbonyl)-HPI
2-(1-dimethylaminocyclobutylcarbonyl)-HPI
2-(2-dimethylaminocyclobutylcarbonyl)-HPI
2-(3-dimethylaminocyclobutylcarbonyl)-HPI
2-(2-methoxycarbonylcyclobutylcarbonyl)-HPI
2-(2-ethoxycarbonylcyclobutylcarbonyl)-HPI
2-(3-methoxycarbonylcyclobutylcarbonyl)-HPI
2-(3-ethoxycarbonylcyclobutylcarbonyl)-HPI
2-cyclobutylcarbonyl-HPI, m.p. 127°
2-(2-ketocyclopentylcarbonyl)-HPI
2-(3-ketocyclopentylcarbonyl)-HPI
2-(1-acetoxycyclopentylcarbonyl)-HPI
2-(2-acetoxycyclopentylcarbonyl)-HPI 2-(3-acetoxycyclopentylcarbonyl)-HPI
2-(2-fluorocyclopentylcarbonyl)-HPI
2-(3-fluorocyclopentylcarbonyl)-HPI
2-(2,2-difluorocyclopentylcarbonyl)-HPI
2-(3,3-difluorocyclopentylcarbonyl)-HPI
2-(2-chlorocyclopentylcarbonyl)-HPI
2-(3-chlorocyclopentylcarbonyl)-HPI
2-(2-methylcyclopentylcarbonyl)-HPI
2-(3-methylcyclopentylcarbonyl)-HPI
2-(1-dimethylaminocyclopentylcarbonyl)-HPI
2-(2-dimethylaminocyclopentylcarbonyl)-HPI
2-(3-dimethylaminocyclopentylcarbonyl)-HPI
2-(2-methoxycarbonylcyclopentylcarbonyl)-HPI
2-(2-ethoxycarbonylcyclopentylcarbonyl)-HPI
2-(3-methoxycarbonylcyclopentylcarbonyl)-HPI
2-(3-ethoxycarbonylcyclopentylcarbonyl)-HPI
2-cyclohexylcarbonyl-HPI, m.p. 136°–138°
2-(1-cyclohexenylcarbonyl)-HPI
2-(2-cyclohexenylcarbonyl)-HPI
2-(3-cyclohexenylcarbonyl)-HPI, m.p. 126°
2-(2-ketocyclohexylcarbonyl)-HPI
2-(3-ketocyclohexylcarbonyl)-HPI
2-(4-ketocyclohexylcarbonyl)-HPI, m.p. 154°
2-(1-acetoxycyclohexylcarbonyl)-HPI
2-(2-acetoxycyclohexylcarbonyl)-HPI
2-(3-acetoxycyclohexylcarbonyl)-HPI
2-(4-acetoxycyclohexylcarbonyl)-HPI
2-(1-formamidocyclohexylcarbonyl)-HPI
2-(2-formamidocyclohexylcarbonyl)-HPI
2-(3-formamidocyclohexylcarbonyl)-HPI
2-(4-formamidocyclohexylcarbonyl)-HPI
2-(1-dimethylaminocyclohexylcarbonyl)-HPI
2-(2-dimethylaminocyclohexylcarbonyl)-HPI
2-(3-dimethylaminocyclohexylcarbonyl)-HPI
2-(4-dimethylaminocyclohexylcarbonyl)-HPI
2-(2,4-bis-dimethylaminocyclohexylcarbonyl)-HPI
2-(3,4-bis-dimethylaminocyclohexylcarbonyl)-HPI
2-(3,5-bis-dimethylaminocyclohexylcarbonyl)-HPI
2-(1-diethylaminocyclohexylcarbonyl)-HPI
2-(2-diethylaminocyclohexylcarbonyl)-HPI
2-(3-diethylaminocyclohexylcarbonyl)-HPI
2-(4-diethylaminocyclohexylcarbonyl)-HPI
2-(3-methylethylaminocyclohexylcarbonyl)-HPI
2-(4-methylethylaminocyclohexylcarbonyl)-HPI
2-(2-fluorocyclohexylcarbonyl)-HPI
2-(3-fluorocyclohexylcarbonyl)-HPI
2-(4-fluorocyclohexylcarbonyl)-HPI
2-(2,2-difluorocyclohexylcarbonyl)-HPI
2-(3,3-difluorocyclohexylcarbonyl)-HPI
2-(4,4-difluorocyclohexylcarbonyl)-HPI
2-(2-chlorocyclohexylcarbonyl)-HPI
2-(3-chlorocyclohexylcarbonyl)-HPI
2-(4-chlorocyclohexylcarbonyl)-HPI
2-(2-bromocyclohexylcarbonyl)-HPI
2-(3-bromocyclohexylcarbonyl)-HPI
2-(4-bromocyclohexylcarbonyl)-HPI
2-(2-methylcyclohexylcarbonyl)-HPI
2-(3-methylcyclohexylcarbonyl)-HPI
2-(4-methylcyclohexylcarbonyl)-HPI
2-(2-methoxycarbonylcyclohexylcarbonyl)-HPI
2-(3-methoxycarbonylcyclohexylcarbonyl)-HPI
2-(4-methoxycarbonylcyclohexylcarbonyl)-HPI
2-(2-ethoxycarbonylcyclohexylcarbonyl)-HPI
2-(3-ethoxycarbonylcyclohexylcarbonyl)-HPI
2-(4-ethoxycarbonylcyclohexylcarbonyl)-HPI
2-cycloheptylcarbonyl-HPI, m.p. 91°
2-(4-dimethylaminocycloheptylcarbonyl)-HPI
2-(4-diethylaminocycloheptylcarbonyl)-HPI
2-(4-fluorocycloheptylcarbonyl)-HPI
2-(4-chlorocycloheptylcarbonyl)-HPI
2-cyclooctylcarbonyl-HPI, m.p. 109°
2-cyclononylcarbonyl-HPI
2-cyclodecylcarbonyl-HPI
2-cycloundecylcarbonyl-HPI, m.p. 150°–151°
2-cyclododecylcarbonyl-HPI
2-bicyclo[2,2,1]heptyl-2-carbonyl-HPI
2-bicyclo[2,2,2]octyl-2-carbonyl-HPI
2-(adamantylcarbonyl)-HPI, m.p. 159°–160°
2-(2-methylbenzoyl)-HPI
2-(3-methylbenzoyl)-HPI, m.p. 124°
2-(4-methylbenzoyl)-HPI, m.p. 183°–184°
2-(4-ethylbenzoyl)-HPI
2-(4-n-propylbenzoyl)-HPI
2-(4-isopropylbenzoyl)-HPI
2-(4-tert.-butylbenzoyl)-HPI, m.p. 198°
2-(4-phenylbenzoyl)-HPI
2-(3,4-dimethylbenzoyl)-HPI
2-(3,5-dimethylbenzoyl)-HPI
2-(3,4-diethylbenzoyl)-HPI
2-(3,5-diethylbenzoyl)-HPI
2-(2-fluorobenzoyl)-HPI, m.p. 129°
2-(3-fluorobenzoyl)-HPI, m.p. 164°–166°
2-(4-fluorobenzoyl)-HPI, m.p. 181°–182°
2-(2-chlorobenzoyl)-HPI
2-(3-chlorobenzoyl)-HPI, m.p. 181°–182°
2-(4-chlorobenzoyl)-HPI, m.p. 214°–215°
2-(2-bromobenzoyl)-HPI
2-(3-bromobenzoyl)-HPI
2-(4-bromobenzoyl)-HPI
2-(2-iodobenzoyl)-HPI
2-(3-iodobenzoyl)-HPI
2-(4-iodobenzoyl)-HPI
2-(2,3-difluorobenzoyl)-HPI
2-(2,4-difluorobenzoyl)-HPI
2-(2,5-difluorobenzoyl)-HPI
2-(2,6-difluorobenzoyl)-HPI
2-(3,4-difluorobenzoyl)-HPI
2-(3,5-difluorobenzoyl)-HPI
2-(3,4-dichlorobenzoyl)-HPI
2-(3,5-dichlorobenzoyl)-HPI, m.p. 165°–166°
2-(3,4-dibromobenzoyl)-HPI
2-(3,5-dibromobenzoyl)-HPI
2-(3,4,5-trifluorobenzoyl)-HPI
2-(2,3,4,5,6-pentafluorobenzoyl)-HPI, m.p. 156°
2-(2-hydroxybenzoyl)-HPI
2-(3-hydroxybenzoyl)-HPI, m.p. 153°
2-(4-hydroxybenzoyl)-HPI, m.p. 243°–245°
2-(3,4-dihydroxybenzoyl)-HPI
2-(3,5-dihydroxybenzoyl)-HPI, m.p. 250°–254° (decomposition)
2-(3,4,5-trihydroxybenzoyl)-HPI
2-(3-methoxybenzoyl)-HPI
2-(4-methoxybenzoyl)-HPI, m.p. 204°–205°
2-(3-acetoxybenzoyl)-HPI
2-(4-acetoxybenzoyl)-HPI
2-(3-trifluoroacetoxybenzoyl)-HPI
2-(4-trifluoroacetoxybenzoyl)-HPI
2-(3,4-dimethoxybenzoyl)-HPI
2-(3,5-dimethoxybenzoyl)-HPI
2-(3,4,5-trimethoxybenzoyl)-HPI
2-(4-phenoxybenzoyl)-HPI
2-(2-dimethylaminobenzoyl)-HPI
2-(3-dimethylaminobenzoyl)-HPI
2-(4-dimethylaminobenzoyl)-HPI, m.p. 225°–226°
2-(2-diethylaminobenzoyl)-HPI
2-(3-diethylaminobenzoyl)-HPI 2-(4-diethylaminobenzoyl)-HPI
2-(4-methylethylaminobenzoyl)-HPI
2-(3,4-bis-dimethylaminobenzoyl)-HPI
2-(3,5-bis-dimethylaminobenzoyl)-HPI
2-(2-formylaminobenzoyl)-HPI
2-(3-formamidobenzoyl)-HPI, m.p. 176°
2-(4-formamidobenzoyl)-HPI, m.p. 207°-208°
2-(2-acetamidobenzoyl)-HPI
2-(3-acetamidobenzoyl)-HPI
2-(4-acetamidobenzoyl)-HPI, m.p. 247°-248°
2-(2-propionamidobenzoyl)-HPI
2-(3-propionamidobenzoyl)-HPI
2-(4-propionamidobenzoyl)-HPI
2-(3-butyramidobenzoyl)-HPI
2-(4-butyramidobenzoyl)-HPI
2-(3,4-bis-formamidobenzoyl)-HPI
2-(3,5-bis-formamidobenzoyl)-HPI
2-(3-isobutyramidobenzoyl)-HPI
2-(4-isobutyramidobenzoyl)-HPI
2-(2-pentanoylaminobenzoyl)-HPI
2-(3-pentanoylaminobenzoyl)-HPI
2-(4-pentanoylaminobenzoyl)-HPI
2-(2-hexanoylaminobenzoyl)-HPI
2-(3-hexanoylaminobenzoyl)-HPI
2-(4-hexanoylaminobenzoyl)-HPI
2-(2-octanoylaminobenzoyl)-HPI
2-(3-octanoylaminobenzoyl)-HPI
2-(4-octanoylaminobenzoyl)-HPI
2-(2-oleoylaminobenzoyl)-HPI
2-(3-oleoylaminobenzoyl)-HPI
2-(4-oleoylaminobenzoyl)-HPI
2-(2-methylmercaptobenzoyl)-HPI
2-(3-methylmercaptobenzoyl)-HPI
2-(4-methylmercaptobenzoyl)-HPI, m.p. 195°
2-(3-ethylmercaptobenzoyl)-HPI
2-(4-ethylmercaptobenzoyl)-HPI
2-(3,4-bis-methylmercaptobenzoyl)-HPI
2-(3,5-bis-methylmercaptobenzoyl)-HPI
2-(3,4,5-tris-methylmercaptobenzoyl)-HPI
2-(4-phenylmercaptobenzoyl)-HPI
2-(2-nitrobenzoyl)-HPI, m.p. 188°-189°
2-(3-nitrobenzoyl)-HPI, m.p. 172°
2-(3,4-dinitrobenzoyl)-HPI, m.p. 219°
2-(3,5-dinitrobenzoyl)-HPI, m.p. 251°-252°
2-(2-trifluoromethylbenzoyl)-HPI
2-(3-trifluoromethylbenzoyl)-HPI, m.p. 148°-149°
2-(4-trifluoromethylbenzoyl)-HPI
2-(2-cyanobenzoyl)-HPI
2-(3-cyanobenzoyl)-HPI
2-(4-cyanobenzoyl)-HPI, m.p. 214°-215°
2-(2-methoxycarbonylbenzoyl)-HPI
2-(3-methoxycarbonylbenzoyl)-HPI
2-(4-methoxycarbonylbenzoyl)-HPI, m.p. 178°
2-(2-ethoxycarbonylbenzoyl)-HPI
2-(3-ethoxycarbonylbenzoyl)-HPI
2-(4-ethoxycarbonylbenzoyl)-HPI
2-(3,4-bis-methoxycarbonylbenzoyl)-HPI
2-(3,5-bis-methoxycarbonylbenzoyl)-HPI
2-(2-azidobenzoyl)-HPI
2-(3-azidobenzoyl)-HPI
2-(4-azidobenzoyl)-HPI
2-(2-methoxysulfonylbenzoyl)-HPI
2-(3-methoxysulfonylbenzoyl)-HPI
2-(4-methoxysulfonylbenzoyl)-HPI
2-(2-ethoxysulfonylbenzoyl)-HPI
2-(3-ethoxysulfonylbenzoyl)-HPI
2-(4-ethoxysulfonylbenzoyl)-HPI
2-(2-chloro-4-nitrobenzoyl)-HPI, m.p. 176°-177°
2-(4-chloro-3-nitrobenzoyl)-HPI, m.p. 192°-194°
2-(3-nitro-4-chlorobenzoyl)-HPI
2-(2-hydroxy-5-chlorobenzoyl)-HPI, m.p. 180°
2-naphthyl-1-carbonyl-HPI, m.p. 135°
2-naphthyl-2-carbonyl-HPI, m.p. 178°
2-(1,2,3,4-tetrahydronaphthyl-1-carbonyl)-HPI
2-(1,2,3,4-tetrahydronaphthyl-2-carbonyl)-HPI
2-(pyrryl-2-carbonyl)-HPI, m.p. 174°
2-(pyrryl-3-carbonyl)-HPI
2-(thienyl-2-carbonyl)-HPI, m.p. 132°-133°
2-(thienyl-3-carbonyl)-HPI, m.p. 142°-143°
2-(3-fluorothienyl-2-carbonyl)-HPI
2-(4-fluorothienyl-2-carbonyl)-HPI
2-(5-fluorothienyl-2-carbonyl)-HPI
2-(3-nitrothienyl-2-carbonyl)-HPI
2-(4-nitrothienyl-2-carbonyl)-HPI
2-(5-nitrothienyl-2-carbonyl)-HPI, m.p. 172°-173°
2-(3-dimethylaminothienyl-2-carbonyl)-HPI
2-(4-dimethylaminothienyl-2-carbonyl)-HPI
2-(3-formylaminothienyl-2-carbonyl)-HPI
2-(4-formylaminothienyl-2-carbonyl)-HPI
2-(3-methylthienyl-2-carbonyl)-HPI
2-(4-methylthienyl-2-carbonyl)-HPI
2-(5-methylthienyl-2-carbonyl)-HPI, m.p. 134°-136°
2-(2-methylthienyl-3-carbonyl)-HPI
2-(4-methylthienyl-3-carbonyl)-HPI
2-(5-methylthienyl-3-carbonyl)-HPI
2-(furyl-2-carbonyl)-HPI, m.p. 120°
2-(furyl-3-carbonyl)-HPI
2-(3-fluorofuryl-2-carbonyl)-HPI
2-(4-fluorofuryl-2-carbonyl)-HPI
2-(5-fluorofuryl-2-carbonyl)-HPI
2-(5-chlorofuryl-2-carbonyl)-HPI
2-(5-bromofuryl-2-carbonyl)-HPI, m.p. 209°
2-(5-nitrofuryl-2-carbonyl)-HPI, m.p. 182°
2-(indolyl-2-carbonyl)-HPI
2-(indolyl-3-carbonyl)-HPI
2-(indolyl-4-carbonyl)-HPI
2-(indolyl-5-carbonyl)-HPI, m.p. 235°
2-(indolyl-6-carbonyl)-HPI
2-(indolyl-7-carbonyl)-HPI
2-(pyrazolyl-3-carbonyl)-HPI
2-(pyrazolyl-4-carbonyl)-HPI
2-(5-methylpyrazolyl-3-carbonyl)-HPI, m.p. 201°
2-(4-methylpyrazolyl-3-carbonyl)-HPI
2-(4-methylimidazolyl-2-carbonyl)-HPI
2-(5-methylimidazolyl-2-carbonyl)-HPI
2-(2-methylimidazolyl-4-carbonyl)-HPI
2-(5-methylimidazolyl-4-carbonyl)-HPI
2-(imidazolyl-2-carbonyl)-HPI
2-(imidazolyl-4-carbonyl)-HPI
2-(thiazolyl-2-carbonyl)-HPI
2-(4-methylthiazolyl-2-carbonyl)-HPI
2-(5-methylthiazolyl-2-carbonyl)-HPI
2-(thiazolyl-4-carbonyl)-HPI, m.p. 154°
2-(2-methylthiazolyl-4-carbonyl)-HPI
2-(5-methylthiazolyl-4-carbonyl)-HPI
2-(thiazolyl-5-carbonyl)-HPI
2-(2-methylthiazolyl-5-carbonyl)-HPI
2-(4-methylthiazolyl-5-carbonyl)-HPI
2-(5-nitrothiazolyl-2-carbonyl)-HPI
2-(2,4-dimethylthiazolyl-5-carbonyl)-HPI, m.p. 162°-163°
2-(benzothiazolyl-2-carbonyl)-HPI
2-(benzothiazolyl-4-carbonyl)-HPI
2-(benzothiazolyl-5-carbonyl)-HPI
2-(isothiazolyl-3-carbonyl)-HPI
2-(4-methylisothiazolyl-3-carbonyl)-HPI 2-(5-methylisothiazolyl-3-carbonyl)-HPI
2-(isothiazolyl-4-carbonyl)-HPI
2-(3-methylisothiazolyl-4-carbonyl)-HPI
2-(5-methylisothiazolyl-4-carbonyl)-HPI
2-(isothiazolyl-5-carbonyl)-HPI
2-(3-methylisothiazolyl-5-carbonyl)-HPI
2-(4-methylisothiazolyl-5-carbonyl)-HPI
2-(oxazolyl-2-carbonyl)-HPI
2-(4-methyloxazolyl-2-carbonyl)-HPI
2-(5-methyloxazolyl-2-carbonyl)-HPI
2-(oxazolyl-4-carbonyl)-HPI
2-(2-methyloxazolyl-4-carbonyl)-HPI
2-(5-methyloxazolyl-4-carbonyl)-HPI
2-(oxazolyl-5-carbonyl)-HPI
2-(2-methyloxazolyl-5-carbonyl)-HPI
2-(4-methyloxazolyl-5-carbonyl)-HPI
2-(isoxazolyl-3-carbonyl)-HPI
2-(4-methylisoxazolyl-3-carbonyl)-HPI
2-(5-methylisoxazolyl-3-carbonyl)-HPI, m.p. 173°–174°
2-(isoxazolyl-4-carbonyl)-HPI
2-(3-methylisoxazolyl-4-carbonyl)-HPI
2-(5-methylisoxazolyl-4-carbonyl)-HPI
2-(isoxazolyl-5-carbonyl)-HPI
2-(3-methylisoxazolyl-5-carbonyl)-HPI
2-(4-methylisoxazolyl-5-carbonyl)-HPI
2-picolinoyl-HPI, hydrobromide, m.p. 163°
2-(3-fluoropicolinoyl)-HPI
2-(4-fluoropicolinoyl)-HPI
2-(5-fluoropicolinoyl)-HPI
2-(6-fluoropicolinoyl)-HPI
2-(3-diethylaminopicolinoyl)-HPI
2-(4-diethylaminopicolinoyl)-HPI
2-(5-diethylaminopicolinoyl)-HPI
2-(6-diethylaminopicolinoyl)-HPI
2-(3-formamidopicolinoyl)-HPI
2-(4-formamidopicolinoyl)-HPI
2-(5-formamidopicolinoyl)-HPI
2-(6-formamidopicolinoyl)-HPI
2-nicotinoyl-HPI, m.p. 172°
2-(2-fluoronicotinoyl)-HPI
2-(4-fluoronicotinoyl)-HPI
2-(5-fluoronicotinoyl)-HPI
2-(6-fluoronicotinoyl)-HPI
2-(2-chloronicotinoyl)-HPI
2-(4-chloronicotinoyl)-HPI, m.p. 158°
2-(5-chloronicotinoyl)-HPI
2-(6-chloronicotinoyl)-HPI
2-(2-hydroxynicotinoyl)-HPI
2-(4-hydroxynicotinoyl)-HPI
2-(5-hydroxynicotinoyl)-HPI
2-(6-hydroxynicotinoyl)-HPI
2-(2-dimethylaminonicotinoyl)-HPI
2-(4-dimethylaminonicotinoyl)-HPI
2-(5-dimethylaminonicotinoyl)-HPI
2-(6-dimethylaminonicotinoyl)-HPI
2-(2-formamidonicotinoyl)-HPI
2-(4-formamidonicotinoyl)-HPI
2-(5-formamidonicotinoyl)-HPI
2-(6-formamidonicotinoyl)-HPI
2-(2-acetamidonicotinoyl)-HPI
2-(4-acetamidonicotinoyl)-HPI
2-(5-acetamidonicotinoyl)-HPI
2-(6-acetamidonicotinoyl)-HPI
2-isonicotinoyl-HPI, m.p. 140°–141°
2-(2,6-dichloroisonicotinoyl)-HPI, m.p. 207°–208°
2-(quinolyl-2-carbonyl)-HPI, m.p. 198°–200°
2-(quinolyl-3-carbonyl)-HPI
2-(quinolyl-4-carbonyl)-HPI
2-(quinolyl-5-carbonyl)-HPI
2-(quinolyl-6-carbonyl)-HPI
2-(quinolyl-7-carbonyl)-HPI
2-(quinolyl-8-carbonyl)-HPI
2-(isoquinolyl-1-carbonyl)-HPI, m.p. 157°
2-(isoquinolyl-3-carbonyl)-HPI
2-(pyridazinyl-3-carbonyl)-HPI
2-(pyridazinyl-4-carbonyl)-HPI
2-(pyrimidinyl-2-carbonyl)-HPI
2-(pyrimidinyl-4-carbonyl)-HPI
2-(pyrimidinyl-5-carbonyl)-HPI
2-(pyrazinyl-2-carbonyl)-HPI, m.p. 153°–154°
2-(purinyl-2-carbonyl)-HPI
2-(purinyl-6-carbonyl)-HPI
2-(purinyl-8-carbonyl)-HPI
2-nalidixinyl-HPI [= 2-(1-ethyl-7-methyl-1,8-naphthyridin-4-one-3-carbonyl)-HPI]
2-(dioxanyl-2-carbonyl)-HPI
2-(4-methylpiperazinyl-1-carbonyl)-HPI, hydrochloride, m.p. 290°
2-(dihydrofuryl-2-carbonyl)-HPI
2-(tetrahydrofuryl-2-carbonyl)HPI
2-(tetrahydrofuryl-3-carbonyl)-HPI
2-(1-methyl-1,2,5,6-tetrahydropyridyl-3-carbonyl)-HPI, hydrochloride, m.p. 211°
2-(1-methyl-1,4,5,6-tetrahydropyridyl-3-carbonyl)-HPI
2-(1-methylpiperidyl-2-carbonyl)-HPI
2-(1-methylpiperidyl-3-carbonyl)-HPI
2-(1-methylpiperidyl-4-carbonyl)-HPI
2-(1-ethylpiperidyl-2-carbonyl)-HPI
2-(1-ethylpiperidyl-3-carbonyl)-HPI
2-(1-ethylpiperidyl-4-carbonyl)-HPI
2-(1-benzylpiperidyl-2-carbonyl)-HPI
2-(1-benzylpiperidyl-3-carbonyl)-HPI
2-(1-benzylpiperidyl-4-carbonyl)-HPI
2-(1-formylpiperidyl-3-carbonyl)-HPI
2-(1-formylpiperidyl-4-carbonyl)-HPI, m.p. 160°
2-(1-acetylpiperidyl-2-carbonyl)-HPI
2-(1-acetylpiperidyl-3-carbonyl)-HPI
2-(1-acetylpiperidyl-4-carbonyl)-HPI
2-(1-hexanoylpiperidyl-2-carbonyl)-HPI
2-(1-hexanoylpiperidyl-3-carbonyl)-HPI
2-(1-hexanoylpiperidyl-4-carbonyl)-HPI
2-(1-octanoylpiperidyl-2-carbonyl)-HPI
2-(1-octanoylpiperidyl-3-carbonyl)-HPI
2-(1-octanoylpiperidyl-4-carbonyl)-HPI
2-(1-oleoylpiperidyl-2-carbonyl)-HPI
2-(1-oleoylpiperidyl-3-carbonyl)-HPI
2-(1-oleoylpiperidyl-4-carbonyl)-HPI
2-[1-(methoxyacetyl)-piperidyl-2-carbonyl]-HPI
2-[1-(methoxyacetyl)-piperidyl-3-carbonyl]-HPI
2-[1-(methoxyacetyl)-piperidyl-4-carbonyl]-HPI
2-[1-(ethoxyacetyl)-piperidyl-2-carbonyl]-HPI
2-[1-(ethoxyacetyl)-piperidyl-3-carbonyl]-HPI
2-[1-(ethoxyacetyl)-piperidyl-4-carbonyl]-HPI
2-(tetrahydropyranyl-2-carbonyl)-HPI
2-(tetrahydropyranyl-3-carbonyl)-HPI
2-(tetrahydropyranyl-4-carbonyl)-HPI, m.p. 172°
2-(chromone-2-carbonyl)-HPI, m.p. 155°–156°
2-(tetrahydrothiopyranyl-2-carbonyl)-HPI
2-(tetrahydrothiopyranyl-3-carbonyl)-HPI
2-(tetrahydrothiopyranyl-4-carbonyl)-HPI, m.p. 168°
2-(1,2,3-thiadiazolyl-4-carbonyl)-HPI
2-(2,1,3-benzothiadiazolyl-5-carbonyl)-HPI, m.p. 144°

EXAMPLE 2

At 140° (bath temperature), 1 ml. of phosphorus trichloride is dropped to a solution of 6.1 g. of HPI and 5.5 g. of 5-chlorosalicylic acid in 50 ml. of chlorobenzene. The mixture is refluxed for one hour, evaporated, the residue is chromatographed over silica gel with chloroform as the eluent, and the product is 2-(5-chloro-2-hydroxybenzoyl)-HPI, m.p. 180° (from isopropanol).

EXAMPLE 3

10.1 g. of HPI, 6.75 g. of isonicotinic acid, and 5.5 g. of silicon tetrachloride are refluxed in 150 ml. of pyridine for one hour. The mixture is then poured on ice, extracted with chloroform, and washed with water. After drying over sodium sulfate and evaporation, 2-(isonicotinoyl)-HPI is obtained, m.p. 140°–141° (from ethanol).

EXAMPLE 4

6.1 g. of HPI and 1.4 g. of formic acid are heated in 100 ml. of toluene for 5 hours; the thus-produced water is distilled off. The mixture is cooled, thus obtaining 2-formyl-HPI, m.p. 206° (from ethanol).

EXAMPLE 5

4.04 g. of HPI and 3.4 g. of cyclohexane-1,2-trans-dicarboxylic acid anhydride are dissolved at 20° in respectively 25 ml. of methylene chloride and then combined. The mixture is allowed to stand, evaporated, and 2-(2-trans-carboxycyclohexylcarbonyl)-HPI is obtained, m.p. 208°–210° (from ethyl acetate/petroleum ether).

Analogously, but with 6 hours of refluxing in dioxane, 2-(2-cis-carboxycyclohexylcarbonyl)-HPI, m.p. 194°–196°, is obtained with cyclohexane-1,2-cis-dicarboxylic acid anhydride.

Analogously, with the use of
cyclobutane-1,2-dicarboxylic acid anhydride
cyclopentane-1,2-dicarboxylic acid anhydride
cycloheptane-1,2-dicarboxylic acid anhydride
phthalic acid anhydride
succinic acid anhydride,
the following final products can be produced:
2-(2-trans-carboxycyclopentylcarbonyl)-HPI
2-(2-trans-carboxycycloheptylcarbonyl)-HPI
2-(2-cis-carboxycyclobutylcarbonyl)-HPI
2-(2-cis-carboxycyclopentylcarbonyl)-HPI
2-(2-cis-carboxycycloheptylcarbonyl)-HPI
2-(2-carboxybenzoyl)-HPI
2-(3-carboxypropionyl)-HPI.

EXAMPLE 6

Analogously to Example 1, the following final products are obtained from the two antipodes (+)-HPI and (−)-HPI and the corresponding acid chlorides:
(+)-2-acetyl-HPI
(−)-2-acetyl-HPI
(+)-2-propionyl-HPI
(−)-2-propionyl-HPI
(+)-2-isobutyryl-HPI
(−)-2-isobutyryl-HPI
(+)-2-trimethylacetyl-HPI
(−)-2-trimethylacetyl-HPI
(+)-2-(3,3-dimethyl-n-butyryl)-HPI
(−)-2-(3,3-dimethyl-n-butyryl)-HPI
(+)-2-heptanoyl-HPI
(−)-2-heptanoyl-HPI
(+)-2-(thienyl-2-mercaptoacetyl)-HPI
(−)-2-(thienyl-2-mercaptoacetyl)-HPI
(+)-2-cyclopropylcarbonyl-HPI
(−)-2-cyclopropylcarbonyl-HPI
(+)-2-cyclobutylcarbonyl-HPI
(−)-2-cyclobutylcarbonyl-HPI
(+)-2-cyclopentylcarbonyl-HPI
(−)-2-cyclopentylcarbonyl-HPI
(+)-2-cyclohexylcarbonyl-HPI, m.p. 108°–110°; $[\alpha] = +145.2°$
(−)-2-cyclohexylcarbonyl-HPI, m.p. 107°–108°; $[\alpha] = -146.9°$
(+)-2-(4-formamidocyclohexylcarbonyl)-HPI
(−)-2-(4-formamidocyclohexylcarbonyl)-HPI
(+)-2-cycloheptylcarbonyl-HPI
(−)-2-cycloheptylcarbonyl-HPI
(+)-2-cyclooctylcarbonyl-HPI
(−)-2-cyclooctylcarbonyl-HPI
(+)-2-(4-methylbenzoyl)-HPI, m.p. 180°–181°; $[\alpha] = +29.2°$
(−)-2-(4-methylbenzoyl)-HPI, m.p. 181°–182°; $[\alpha] = -28.5°$
(+)-2-(4-tert.-butylbenzoyl)-HPI, m.p. 181°–182°; $[\alpha] = +21.5°$
(−)-2-(4-tert.-butylbenzoyl)-HPI, m.p. 168°–169°; $[\alpha] = -20.5°$
(+)-2-(2-fluorobenzoyl)-HPI, m.p. 155°–156°; $[\alpha] = +49.1°$
(−)-2-(2-fluorobenzoyl)-HPI, m.p. 159°–161°; $[\alpha] = -49.9°$
(+)-2-(3-fluorobenzoyl)-HPI, m.p. 156°–158° (sintering at 148°); $[\alpha] = +40.2°$
(−)-2-(3-fluorobenzoyl)-HPI, m.p. 156; $[\alpha] = -41.6°$
(+)-2-(4-fluorobenzoyl)-HPI, m.p. 200°–201°; $[\alpha] = +33.5°$
(−)-2-(4-fluorobenzoyl)-HPI, m.p. 202°–203°; $[\alpha] = -32.6°$
(+)-2-(3-chlorobenzoyl)-HPI
(−)-2-(3-chlorobenzoyl)-HPI
(+)-2-(4-chlorobenzoyl)-HPI, m.p. 231°–232°; $[\alpha] = +20.4°$
(−)-2-(4-chlorobenzoyl)-HPI, m.p. 233°–234°; $[\alpha] = -20.7°$
(+)-2-(3-hydroxybenzoyl)-HPI
(−)-2-(3-hydroxybenzoyl)-HPI
(+)-2-(4-hydroxybenzoyl)-HPI
(−)-2-(4-hydroxybenzoyl)-HPI
(+)-2-(4-methoxybenzoyl)-HPI, m.p. 215°; $[\alpha] = +19.8°$
(−)-2-(4-methoxybenzoyl)-HPI, m.p. 216°; $[\alpha] = -18.7°$
(+)-2-(3-dimethylaminobenzoyl)-HPI
(−)-2-(3-dimethylaminobenzoyl)-HPI
(+)-2-(4-dimethylaminobenzoyl)-HPI
(−)-2-(4-dimethylaminobenzoyl)-HPI
(+)-2-(4-diethylaminobenzoyl)-HPI
(−)-2-(4-diethylaminobenzoyl)-HPI
(+)-2-(2-formamidobenzoyl)-HPI
(−)-2-(2-formamidobenzoyl)-HPI
(+)-2-(3-formamidobenzoyl)-HPI
(−)-2-(3-formamidobenzoyl)-HPI
(+)-2-(4-formamidobenzoyl)-HPI, m.p. 193°; $[\alpha] = +8.6°$
(−)-2-(4-formamidobenzoyl)-HPI, m.p. 193°; $[\alpha] = -8.4°$
(+)-2-(2-acetamidobenzoyl)-HPI
(−)-2-(2-acetamidobenzoyl)-HPI
(+)-2-(3-acetamidobenzoyl)-HPI (−)-2-(3-acetamidobenzoyl)-HPI
(+)-2-(4-acetamidobenzoyl)-HPI
(−)-2-(4-acetamidobenzoyl)-HPI
(+)-2-(2-nitrobenzoyl)-HPI
(−)-2-(2-nitrobenzoyl)-HPI
(+)-2-(3-nitrobenzoyl)-HPI, m.p. 139°; [α] = + 2.9°(from the (−)-base)
(−)-2-(3-nitrobenzoyl)-HPI, m.p. 139°; [α] = − 2.9°(from the (+)-base)
(+)-2-(4-nitrobenzoyl)-HPI, m.p. 233°-224°; [α] = + 18.5°
(−)-2-(4-nitrobenzoyl)-HPI, m.p. 223°-224°; [α] = − 21.4°
(+)-2-(thienyl-2-carbonyl)-HPI
(−)-2-(thienyl-2-carbonyl)-HPI
(+)-2-(thienyl-3-carbonyl)-HPI
(−)-2-(thienyl-3-carbonyl)-HPI
(+)-2-(5-methylthienyl-2-carbonyl)-HPI
(−)-2-(5-methylthienyl-2-carbonyl)-HPI
(+)-2-(furyl-2-carbonyl)-HPI
(−)-2-(furyl-2-carbonyl)-HPI
(+)-2-picolinoyl-HPI
(−)-2-picolinoyl-HPI
(+)-2-nicotinoyl-HPI, m.p. 148°; [α] = + 25.5°
(−)-2-nicotinoyl-HPI, m.p. 156°; [α] = − 28.4°
(+)-2-isonicotinoyl-HPI
(−)-2-isonicotinoyl-HPI
(+)-2-nicotinoyl-HPI-1'-N-oxide
(−)-2-nicotinoyl-HPI-1'-N-oxide
(+)-2-(tetrahydropyranyl-4-carbonyl)-HPI
(−)-2-(tetrahydropyranyl-4-carbonyl)-HPI
(+)-2-(tetrahydrothiopyranyl-4-carbonyl)-HPI
(−)-2-(tetrahydrothiopyranyl-4-carbonyl)-HPI
(+)-2-(N-formylpiperidyl-4-carbonyl)-HPI
(−)-2-(N-formylpiperidyl-4-carbonyl)-HPI.

EXAMPLE 7

3.8 g. of 3-trifluoromethylbenzoyl fluoride in 50 ml. of chloroform is added dropwise to 4.04 g. of HPI and 2.8 ml. of triethylamine in 50 ml. of chloroform. The reaction mixture is maintained for one hour at 20°, extracted with dilute hydrochloric acid and water, evaporated, and 2-(3-trifluoromethylbenzoyl)-HPI is thus obtained, m.p. 148°-149° (from ethanol).

EXAMPLE 8

Analogously to Example 1, 2-(4-nitrobenzoyl)-HPI (m.p. 212°-213°) is produced from HPI and p-nitrobenzoyl bromide in chloroform in the presence of triethylamine after a reaction period of two hours.

EXAMPLE 9

Analogously to Example 1, 2-(4-nitrobenzoyl)-HPI (m.p. 212°-213°) is obtained at 40° (2 hours) from HPI and p-nitrobenzoyl iodide in chloroform in the presence of triethylamine.

EXAMPLE 10

Under nitrogen at 20°, 12 ml. of 20% butyllithium solution in hexane is added dropwise to 8.5 g. of N-(2-chloroacetyl-1,2,3,4-tetrahydroisoquinolinyl-1-methyl)-4-fluorobenzamide [obtainable by hydrogenation of 1-cyano-2-(4-fluorobenzoyl)-1,2-dihydroisoquinoline on Raney nickel at 100° and under 250 atmospheres, and reaction of the thus-formed N-(1,2,3,4-tetrahydroisoquinolinyl-1-methyl)-4-fluorobenzamide with chloroacetyl chloride in chloroform in the presence of triethylamine in 300 ml. abs. THF]. The mixture is stirred for 2 hours at 20° and refluxed for another 12 hours. After the addition of water, the solvent is removed and the residue taken up in chloroform. Then, the mixture is extracted with water, dried, and evaporated, thus obtaining 2-(4-fluorobenzoyl)-HPI, m.p. 181°-182° (from methanol).

Analogously, (−)-2-(4-fluorobenzoyl)-HPI can be obtained from 8.5 g. of (+)-N-(2-chloroacetyl-1,2,3,4-tetrahydroisoquinolinyl-1-methyl)-4-fluorobenzamide and butyllithium; m.p. 202°-203°; [α] = − 32.6°.

In an analagous manner, 2-(4-methylbenzoyl)-HPI, m.p. 183°-184°, is produced from N-(2-bromoacetyl-1,2,3,4-tetrahydroisoquinolinyl-1-methyl)-4-methylbenzamide or from N-(2-iodoacetyl-1,2,3,4-tetrahydroisoquinolinyl-1-methyl)-4-methylbenzamide or from N-(2-p-toluenesulfonyloxyacetyl-1,2,3,4-tetrahydroisoquinolinyl-1-methyl)-p-methylbenzamide and butyllithium.

Furthermore, 2-cyclohexylcarbonyl-HPI, m.p. 136°-138° is obtained analogously from N-(2-chloroacetyl-1,2,3,4-tetrahydroisoquinolinyl-1-methyl)-cyclohexylcarboxylic acid amide with butyllithium.

EXAMPLE 11

15 g. of a nickel-aluminum alloy (1:1) is introduced in incremental portions and under agitation into 200 ml. of 20% sodium hydroxide solution within 5 minutes; the mixture is maintained at 80° for 45 minutes, then allowed to settle, decanted off, washed with water, and 1,000 ml. of 1% (−)-tartaric acid solution is added thereto, adjusted to pH 5 with 1N sodium hydroxide solution. The mixture is heated under agitation for 90 minutes to 80°, decanted, and washed with water and methanol. The thus-obtained (−)-tartaric acid — Raney nickel catalyst is added to a solution of 322 mg. of 2-(4-fluorobenzoyl)-4-oxo-2,3,6,7-tetrahydro-4H-pyrazino[2,1-a]isoquinolaine (obtainable by dehydrogenation of (±)- or of (+)-2-(4-fluorobenzoyl)-HPI with sulfur) in 40 ml. of methanol. The reaction mixture is hydrogenated under normal pressure and at room temperature. After the catalyst has been filtered off and the solvent evaporated, (−)-2-(4-fluorobenzoyl)-HPI is obtained in 23% optical purity; m.p. 190°-193°; [α] = − 7.5°

Analogously, (−)-2-cyclohexylcarbonyl-HPI is obtained in 20% optical purity; m.p. 122°-127°; [α] = − 29.3°; from 2-cyclohexylcarbonyl-4-oxo-2,3,6,7-tetrahydro-4H-pyrazino[2,1-a]isoquinoline (m.p. 140°-141°).

EXAMPLE 12

Analogously to Example 11, 322 mg. of 2-(4-fluorobenzoyl)-4-oxo-2,3,6,7-tetrahydro-4H-pyrazino[2,1-a]isoquinoline is hydrogenated in 40 ml. of methanol in the presence of 300 mg. of Raney nickel, thus obtaining racemic 2-(4-fluorobenzoyl)-HPI, m.p. 181°-182°.

Analogously, 2-cyclohexylcarbonyl-HPI, m.p. 136°-138°, is produced from 2-cyclohexylcarbonyl-4-oxo-2,3,6,7-tetrahydro-4H-pyrazino[2,1-a]isoquinoline.

EXAMPLE 13

A solution of 67.7 g. of 2-(4-nitrobenzoyl)-HPI in 1,500 ml. of methanol is hydrogenated on 12 g. of 5% palladium charcoal at 20° under normal pressure. The catalyst is filtered off, the filtrate is evaporated, and the residue yields 2-(4-aminobenzoyl)-HPI, m.p. 212°-213° (from ethanol); hydrochloride, m.p. 165°-166° (decomposition); sulfate, m.p. 234°-235°; isethionate, m.p. 233°-234°.

Analogously, the following products are obtained by hydrogenation of the corresponding nitro compounds:
2-aminoacetyl-HPI
2-(2-aminopropionyl)-HPI
2-(3-aminopropionyl)-HPI
2-(2-amino-n-butyryl)-HPI
2-(4-amino-n-butyryl)-HPI
2-(2-amino-n-valeryl)-HPI
2-(5-amino-n-valeryl)-HPI
2-(3-aminophenoxyacetyl)-HPI
2-(4-aminophenoxyacetyl)-HPI
2-(2-aminocyclopropylcarbonyl)-HPI
2-(1-aminocyclobutylcarbonyl)-HPI
2-(2-aminocyclobutylcarbonyl)-HPI
2-(3-aminocyclobutylcarbonyl)-HPI
2-(1-aminocyclopentylcarbonyl)-HPI
2-(2-aminocyclopentylcarbonyl)-HPI
2-(3-aminocyclopentylcarbonyl)-HPI
2-(1-aminocyclohexylcarbonyl)-HPI
2-(2-aminocyclohexylcarbonyl)-HPI
2-(3-aminocyclohexylcarbonyl)-HPI
cis-2-(4-aminocyclohexylcarbonyl)-HPI, amorphous; IR: 3500, 3300 and 1645 cm$^{-1}$
trans-2-(4-aminocyclohexylcarbonyl)-HPI, m.p. 284°
2-(4-aminocycloheptylcarbonyl)-HPI
2-(2-aminobenzoyl)-HPI, hydrobromide, m.p. 279°-280°
2-(3-aminobenzoyl)-HPI, m.p. 161°-162°
(+)-2-(3-aminobenzoyl)-HPI, m.p. 164°-165°; [α] = + 35.9° (from the (−)-nitro antipode)
(−)-2-(3-aminobenzoyl)-HPI, m.p. 164°-165°; [α] = − 36.5° (from the (+)-nitro antipode)
(+)-2-(4-aminobenzoyl)-HPI, m.p. 231°-232°; [α] = + 23.1°; hydrobromide: m.p. starting with 193° (decomposition); isethionate: m.p. 200°-210°; [α] = + 16.0°
(−)-2-(4-aminobenzoyl)-HPI, m.p. 231°-232°; [α] = − 23.0°; hydrobromide: m.p. starting with 205° (decomposition); isethionate: m.p. 200°-210°; [α] = − 16.3°
2-(3,4-diaminobenzoyl)-HPI, m.p. 143°
2-(3,5-diaminobenzoyl)-HPI, m.p. 235°-236°
2-(2-chloro-4-aminobenzoyl)-HPI, m.p. 145°; hydrochloride: m.p. 181°-182°
2-(2-chloro-5-aminobenzoyl)-HPI
2-(3-chloro-4-aminobenzoyl)-HPI
2-(3-chloro-5-aminobenzoyl)-HPI
2-(2-amino-3-chlorobenzoyl)-HPI
2-(2-amino-4-chlorobenzoyl)-HPI
2-(2-amino-5-chlorobenzoyl)-HPI
2-(3-amino-4-chlorobenzoyl)-HPI; hydrobromide: m.p. 208°-210°
2-(3-aminothienyl-2-carbonyl)-HPI
2-(4-aminothienyl-2-carbonyl)-HPI
2-(4-aminotetrahydrothiopyranyl-4-carbonyl)-HPI, m.p. 157°-158°
2-(4-aminonicotinoyl)-HPI
2-(5-aminonicotinoyl)-HPI.

EXAMPLE 14

2.4 g. of acetyl chloride in 100 ml. of chloroform is added to 9.6 g. of 2-(4-aminobenzoyl)-HPI and 3.1 g. of triethylamine in 300 ml. of chloroform; the mixture is allowed to stand for 2 hours at 20°. Thereafter, another 2.4 g. of acetyl chloride is added, along with 3.1 g. of triethylamine, and the mixture is refluxed for 3 hours, whereupon it is washed with dilute hydrochloric acid and water. After the solvent has been evaporated, 2-(4-acetamidobenzoyl)-HPI is obtained, m.p. 247°-248° (from acetone).

Analogously, the following compounds are produced by acylation:
2-acetamidoacetyl-HPI
2-(1-acetamidocyclohexylcarbonyl)-HPI
2-(2-acetamidocyclohexylcarbonyl)-HPI
2-(3-acetamidocyclohexylcarbonyl)-HPI
2-(4-acetamidocyclohexylcarbonyl)-HPI
2-(4-propionamidocyclohexylcarbonyl)-HPI
2-(4-pentanoylaminocyclohexylcarbonyl)-HPI
2-(4-hexanoylaminocyclohexylcarbonyl)-HPI
2-(4-octanoylaminocyclohexylcarbonyl)-HPI
2-(4-oleoylaminocyclohexylcarbonyl)-HPI
2-(2-sulfaminoacetyl)-HPI (with chlorosulfonic acid)
2-(4-sulfaminocyclohexylcarbonyl)-HPI
2-(3-sulfaminobenzoyl)-HPI
2-(4-sulfaminobenzoyl)-HPI
2-(1-sulfopiperidyl-4-carbonyl)-HPI.

EXAMPLE 15

A solution of 3.5 g. of 2-(4-methylnitrosaminobenzoyl)-HPI (produced by introducing the nitroso group into 2-(4-methylaminobenzoyl)-HPI) in 5 ml. of acetic acid is gradually added under vigorous agitation to 2.7 g. of zinc dust in 5 ml. of water. The mixture is stirred for 2 hours at 20°, heated to 80°, and filtered in the hot condition. The residue is washed with 5% hydrochloric acid, and the combined filtrates are rendered alkaline and extracted with chloroform. The extract is washed neutral with water and evaporated, thus obtaining 2-[4-(1-methylhydrazino)-benzoyl]-HPI.

Analogously, the following products are obtained:
2-[2-(1-methylhydrazino)-benzoyl]-HPI
2-[3-(1-methylhydrazino)-benzoyl]-HPI
2-[4-(1-ethylhydrazino)-benzoyl]-HPI.

EXAMPLE 16

8 ml. of 30% strength hydrogen peroxide and 0.8 ml. of 6N NaOH are added to 5 g. of 2-(4-cyanobenzoyl)-HPI in 20 ml. of ethanol. The mixture heats up while giving off oxygen. The temperature is maintained for 1 hour between 40° and 50°; then the mixture is cooled and combined with 5 ml. of water, thus producing 2-(4-carboxamidobenzoyl)-HPI.

Analogously, 2-(3-carboxamidobenzoyl)-HPI is prepared from 2-(3-cyanobenzoyl)-HPI.

EXAMPLE 17

A mixture of 8 g. of 2-(4-methoxycarbonylbenzoyl)-HPI and 500 ml. of 10% sodium hydroxide solution is agitated for 12 hours at 20°. The reaction mixture is filtered off from the undissolved matter, acidified with hydrochloric acid, and extracted with chloroform. The residue is purified by chromatography on silica gel (eluent: chloroform/methanol), thus obtaining 2-(4-carboxybenzoyl)-HPI, m.p. 251°.

Analogously, the following compounds are obtained by alkaline saponification:
2-(2-carboxycyclopropylcarbonyl)-HPI
2-(2-carboxycyclobutylcarbonyl)-HPI
2-(3-carboxycyclobutylcarbonyl)-HPI
2-(2-carboxycyclopentylcarbonyl)-HPI
2-(3-carboxycyclopentylcarbonyl)-HPI
trans-2-(2-carboxycyclohexylcarbonyl)-HPI, m.p. 208°-210° cis-2-(2-carboxycyclohexylcarbonyl)-HPI, m.p. 194°–196°
2-(3-carboxycyclohexylcarbonyl)-HPI
2-(4-carboxycyclohexylcarbonyl)-HPI
2-(2-carboxybenzoyl)-HPI
2-(3-carboxybenzoyl)-HPI
2-(3,4-dicarboxybenzoyl)-HPI
2-(3,5-dicarboxybenzoyl)-HPI.

EXAMPLE 18

A solution of 32 g. of 2-(4-hydroxybenzoyl)-HPI in 150 ml. of methanol/water (10:1) is combined with an excess of ethereal diazomethane solution until a slight yellow coloring remains. The mixture is then evaporated, the residue taken up in ether, washed with dilute sodium hydroxide solution and water, dried with sodium sulfate, evaporated, and the product thus obtained is 2-(4-methoxybenzoyl)-HPI, m.p. 204°–205°.

EXAMPLE 19

At −5° to −10°, 7.5 g. of boron tribromide is added dropwise to 5.4 g. of 2-(4-methoxybenzoyl)-HPI in 100 ml. of methylene chloride. The mixture is agitated for one hour at 20° and poured on ice. The organic phase is separated, and the aqueous phase is extracted several times with methylene chloride. The combined organic phases are dried over sodium sulfate and then evaporated. From the residue, 2-(4-hydroxybenzoyl)-HPI is obtained, m.p. 243°–245° (from ethanol).

EXAMPLE 20

A mixture of 3.22 g. of 2-(4-hydroxybenzoyl)-HPI, 1.02 g. of acetic anhydride, and 100 ml. of pyridine is refluxed for 3 hours; the mixture is then poured on ice, extracted with ether, washed with water, and dried over sodium sulfate, yielding 2-(4-acetoxybenzoyl)-HPI.

EXAMPLE 21

A mixture of 4.8 g. of 2-(4-aminobenzoyl)-HPI and 1.5 g. of 33% formaldehyde solution in 200 ml. of methanol is hydrogenated on 0.5 g. of 5% palladium charcoal. Thereafter, the mixture is filtered, the solvent removed by evaporation, and the residue purified by chromatography on silica gel (eluent: chloroform), thus obtaining 2-(4-methylaminobenzoyl)-HPI, m.p. 220°.

EXAMPLE 22

Analogously to Example 21, 2-(4-dimethylaminobenzoyl)-HPI, m.p. 225°–226°, is produced from 4.8 g. of 2-(4-aminobenzoyl)-HPI and 4 g. of 33% formaldehyde solution.

EXAMPLE 23

Within 2 hours, 3.2 g. of 2-(4-aminobenzoyl)-HPI in 100 ml. of dioxane is combined, under the exclusion of moisture, with 2.5 g. of dimethyl sulfate and then stirred for 15 hours at 100°. The mixture is then cooled, 1.4 g. of potassium hydroxide in 5 ml. of water is added thereto, and the mixture is extracted with chloroform. After evaporation, 2-(4-dimethylaminobenzoyl)-HPI is obtained, m.p. 225°–226°.

EXAMPLE 24

10.4 g. of 2-(4-trifluoroacetamidobenzoyl)-HPI (obtainable from 2-(4-aminobenzoyl)-HPI with trifluoroacetic anhydride/triethylamin) is heated with 34.2 g. of methyl iodide in 300 ml. of acetone almost to the boiling point; then, 13.4 g. of pulverized potassium hydroxide is added thereto and the mixture refluxed for 5 minutes, whereupon the mixture is evaporated, combined with water, and stirred for 2 hours at 20°. The mixture is then extracted with chloroform, washed with water, and evaporated, yielding 2-(4-methylaminobenzoyl)-HPI, m.p. 220°.

If the methyl iodide is not removed prior to hydrolysis, 2-(4-dimethylaminobenzoyl)-HPI is obtained, m.p. 225°–226°.

EXAMPLE 25

Analogously to Example 19, 2-(4-mercaptobenzoyl)-HPI is obtained from 2-(4-methylmercaptobenzoyl)-HPI and boron tribromide.

Analogously, 2-(2-mercaptobenzoyl)-HPI and 2-(3-mercaptobenzoyl)-HPI can be produced.

EXAMPLE 26

(a) At 0°, 1.15 g. of sodium borohydride is added in incremental portions to 6.5 g. of 2-(4-oxocyclohexylcarbonyl)-HPI in 100 ml. of ethanol. The mixture is agitated for 12 hours at 20°, poured on ice, and 2-(4-hydroxycyclohexylcarbonyl)-HPI is thus produced as a mixture of isomers.

(b) Under nitrogen at −70°, 24 ml. of a 0.5-molar solution of potassium tris(sec.-butyl)borohydride in THF is added to a solution of 3.25 g. of 2-(4-oxocyclohexylcarbonyl)-HPI in 35 ml. of absolute THF. After 3 hours, the mixture is combined with 35 ml. of water, allowed to warm up to 20°, and worked up with chloroform. Chromatographic purification on silica gel with chloroform yields cis-2-(4-hydroxycyclohexylcarbonyl)-HPI, m.p. 162°–163°.

EXAMPLE 27

6.5 g. of 2-(4-oxocyclohexylcarbonyl)-HPI in 100 ml. of methanol is hydrogenated in the presence of 2 g. of Raney nickel at 50° and under 100 atmospheres to saturation. The reaction product is filtered off from the catalyst, the solvent is evaporated, and 2-(4-hydroxycyclohexylcarbonyl)-HPI is thus obtained as a mixture of isomers.

EXAMPLE 28

3.16 g. of 2-(4-oxocyclohexylcarbonyl)-HPI in 100 ml. of methanol, saturated at 10° with ammonia, is hydrogenated in the presence of 1 g. of Raney nickel at 70° and under 100 atmospheres for 10 hours. The catalyst is filtered off, the solvent is evaporated, and the residue is dissolved in ethanol. After adding HBr in ethanol and then combining the mixture with ether, trans-2-(4-aminocyclohexylcarbonyl)-HPI hydrobromide is crystallized, m.p. 284°. From the filtrate, by adding NaOH, extraction with chloroform, and evaporation, cis-2-(4-aminocyclohexylcarbonyl)-HPI is obtained.

EXAMPLE 29

At room temperature and under 5 atmospheres, 3.1 g. of 2-(4-oximinocyclohexylcarbonyl)-HPI (m.p. 194°; obtainable from 2-(4-oxocyclohexylcarbonyl)-HPI and hydroxylamine) is hydrogenated in 100 ml. of ethanol in the presence of 4 g. of Raney nickel until saturation. Evaporation yields 2-(4-aminocyclohexylcarbonyl)-HPI (mixture of isomers).

EXAMPLE 30

A solution of 5.5 g. of 2-isonicotinoyl-HPI and 6.3 g. of 3-chloroperbenzoic acid (50%) is allowed to stand in methylene chloride overnight at 20°. Then, ammonia is introduced to saturation, the mixture is filtered and washed with methylene chloride. Evaporation of the filtrate yields 2-isonicotinoyl-HPI-1'-N-oxide, m.p. 250° (from ethanol).

Analogously, 2-nicotinoyl-HPI-1'-N-oxide, m.p. 178°, is obtained from 2-nicotinoyl-HPI.

Analogously, the corresponding N-oxides can be obtained from the dialkylamino compounds recited in Example 1, for example 2-(4-dimethylaminobenzoyl)-HPI-N-oxide.

EXAMPLE 31

3.2 g. of 2-(4-dimethylaminobenzoyl)-HPI and 5 g. of methyl iodide is heated overnight in 600 ml. of acetonitrile to 75°; the solvent is evaporated, the thus-produced mixture is purified on silica gel (eluent: chloroform/methanol), the obtaining the methoiodide of 2-(4-dimethylaminobenzoyl)-HPI, m.p. 215°–216° (from ethanol).

EXAMPLE 32

2.1 g. of 1-aminocyclohexane-1-carboxylic acid is combined with 6.3 g. of trifluoroacetic anhydride. At 0°, 2 g. of HPI and 2.3 g. of triethylamine in 20 ml. of methyle chloride are added thereto, and the mixture is heated to 30°. After one hour, the reaction mixture is poured into water, the organic phase is separated, washed with sodium hydroxide solution and water, dried, and evaporated, thus producing 2-(1-aminocyclohexyl-1-carbonyl)-HPI, m.p. 146° (from benzene).

Analogously, the following compounds are obtained:
2-methylaminoacetyl-HPI
2-ethylaminoacetyl-HPI
2-(2-methylaminopropionyl)-HPI
2-(2-ethylaminopropionyl)-HPI
2-(3-methylaminopropionyl)-HPI
2-(3-ethylaminopropionyl)-HPI
2-(2-methylamino-n-butyryl)-HPI
2-(4-methylamino-n-butyryl)-HPI
2-(4-ethylamino-n-butyryl)-HPI
2-(2-methylamino-n-valeryl)-HPI
2-(5-methylamino-n-valeryl)-HPI
2-(1-methylaminocyclobutylcarbonyl)-HPI
2-(2-methylaminocyclobutylcarbonyl)-HPI
2-(3-methylaminocyclobutylcarbonyl)-HPI
2-(1-ethylaminocyclobutylcarbonyl)-HPI
2-(2-ethylaminocyclobutylcarbonyl)-HPI
2-(3-ethylaminocyclobutylcarbonyl)-HPI
2-(1-methylaminocyclopentylcarbonyl)-HPI
2-(2-methylaminocyclopentylcarbonyl)-HPI
2-(3-methylaminocyclopentylcarbonyl)-HPI
2-(1-ethylaminocyopentylcarbonyl)-HPI
2-(2-ethylaminocyclopentylcarbonyl)-HPI
2-(3-ethylaminocyclopentylcarbonyl)-HPI
2-(2,4-diaminocyclohexylcarbonyl)-HPI
2-(3,4-diaminocyclohexylcarbonyl)-HPI
2-(3,5-diaminocyclohexylcarbonyl)-HPI
2-(1-methylaminocyclohexylcarbonyl)-HPI
2-(2-methylaminocyclohexylcarbonyl)-HPI
2-(3-methylaminocyclohexylcarbonyl)-HPI
2-(4-methylaminocyclohexylcarbonyl)-HPI
2-(1-ethylaminocyclohexylcarbonyl)-HPI
2-(2-ethylaminocyclohexylcarbonyl)-HPI
2-(3-ethylaminocyclohexylcarbonyl)-HPI
2-(4-ethylaminocyclohexylcarbonyl)-HPI
2-(2,4-bis-methylaminocyclohexylcarbonyl)-HPI
2-(3,4-bis-methylaminocyclohexylcarbonyl)-HPI
2-(3,5-bis-methylaminocyclohexylcarbonyl)-HPI
2-(2,4-bis-ethylaminocyclohexylcarbonyl)-HPI
2-(3,4-bis-ethylaminocyclohexylcarbonyl)-HPI
2-(3,5-bis-ethylaminocyclohexylcarbonyl)-HPI
2-(4-methylaminocycloheptylcarbonyl)-HPI
2-(4-ethylaminocycloheptylcarbonyl)-HPI
2-(2-methylaminobenzoyl)-HPI
2-(3-methylaminobenzoyl)-HPI
2-(4-methylaminobenzoyl)-HPI, m.p. 220°
2-(2-ethylaminobenzoyl)-HPI
2-(3-ethylaminobenzoyl)-HPI
2-(4-ethylaminobenzoyl)-HPI
2-(3,4-bis-methylaminobenzoyl)-HPI
2-(3,5-bis-methylaminobenzoyl)-HPI
2-(3,4-bis-ethylaminobenzoyl)-HPI
2-(3,5-bis-ethylaminobenzoyl)-HPI
2-(3-aminopicolinoyl)-HPI
2-(4-aminopicolinoyl)-HPI
2-(5-aminopicolinoyl)-HPI
2-(6-aminopicolinoyl)-HPI
2-(3-methylaminopicolinoyl)-HPI
2-(4-methylaminopicolinoyl)-HPI
2-(5-methylaminopicolinoyl)-HPI
2-(6-methylaminopicolinoyl)-HPI
2-(2-aminonicotinoyl)-HPI
2-(4-aminonicotinoyl)-HPI
2-(5-aminonicotinoyl)-HPI
2-(6-aminonicotinoyl)-HPI
2-(2-methylaminonicotinoyl)-HPI
2-(4-methylaminonicotinoyl)-HPI
2-(5-methylaminonicotinoyl)-HPI
2-(6-methylaminonicotinoyl)-HPI
2-(benzimidazolyl-2-carbonyl)-HPI
2-(pyrrolinyl-2-carbonyl)-HPI
2-(pyrrolidinyl-2-carbonyl)-HPI
2-(pyrrolidinyl-3-carbonyl)-HPI
2-(1,2,3,4-tetrahydropyridyl-1-carbonyl)-HPI
2-(1,2,3,4-tetrahydropyridyl-2-carbonyl)-HPI
2-(piperidyl-1-carbonyl)-HPI
2-(piperidyl-2-carbonyl)-HPI
2-(piperidyl-3-carbonyl)-HPI
2-(piperidyl-4-carbonyl)-HPI, monohydrate, m.p. 146°–147°
2-(1,2,3,4-tetrahydroquinolyl-3-carbonyl)-HPI
2-(1,2,3,4-tetrahydroquinolyl-4-carbonyl)-HPI
2-(1,2,3,4-tetrahydroisoquinolyl-1-carbonyl)-HPI
2-(1,2,3,4-tetrahydroisoquinolyl-3-carbonyl)-HPI
2-(1,2,3,4-tetrahydroisoquinolyl-4-carbonyl)-HPI.

If the organic phase is not washed with sodium hydroxide solution, the corresponding trifluoroacetylamino compounds are also produced, for example:
2-(1-trifluoroacetamidocyclohexylcarbonyl)-HPI.

EXAMPLE 33

4.04 g. of HPI and 1.5 g. of acetic acid are added to a suspension of 4.2 g. of the Leuchs anhydride of 4-aminotetrahydrothiopyran-4-carboxylic acid (1,3-diox-o-2-oxa-8-thiaspiro[4,5]decane; obtainable from this acid with phosgene) in 300 ml. of chloroform. The reaction mixture is refluxed for 24 hours, cooled, filtered, the filtrate washed with dilute sodium hydroxide solution and water, and evaporated, thus obtaining 2-(4-aminotetrahydrothiopyran-4-carbonyl)-HPI, m.p. 157°–158° (from ethyl acetate/ether/petroleum ether).

EXAMPLE 34

In an autoclave, 3.26 g. of 2-(4-oxocyclohexylcarbonyl)-HPI, 0.2 ml. of water, and 3.2 g. of sulfur tetrafluoride are shaken in 50 ml. of methylene chloride for 24 hours at 30°. The mixture is the poured into dilute sodium carbonate solution, washed with water, dried over sodium sulfate, and evaporated, thus producing 2-(4,4-difluorocyclohexylcarbonyl)-HPI.

EXAMPLE 35

3.4 g. of 2-(4-mercaptobenzoyl)-HPI is heated with 40 ml. of nitric acid (d = 1.2) on a water bath. After the first vigorous reaction has died down, the mixture is evaporated, thus obtaining 2-(4-sulfobenzoyl)-HPI.

Analogously, 2-(2-sulfobenzoyl)-HPI and 2-(3-sulfobenzoyl)-HPI are produced by oxidation of the corresponding mercapto compounds.

EXAMPLE 36

Analogously to Example 17, 8 g. of 2-(4-acetoxybenzoyl)-HPI is saponified in the presence of 10% sodium hydroxide solution, thus obtaining 2-(4-hydroxybenzoyl)-HPI, m.p. 243°–245°.

In an analogous manner, the following final products are produced by saponification of the corresponding acetates:

2-(2-hydroxyacetyl)-HPI
2-(2-hydroxycyclopropylcarbonyl)-HPI
2-(1-hydroxycyclobutylcarbonyl)-HPI
2-(2-hydroxycyclobutylcarbonyl)-HPI
2-(3-hydroxycyclobutylcarbonyl)-HPI
2-(1-hydroxycyclopentylcarbonyl)-HPI
2-(2-hydroxycyclopentylcarbonyl)-HPI
2-(3-hydroxycyclopentylcarbonyl)-HPI
2-(1-hydroxycyclohexylcarbonyl)-HPI
2-(2-hydroxycyclohexylcarbonyl)-HPI
2-(3-hydroxycyclohexylcarbonyl)-HPI
2-(4-hydroxycyclohexylcarbonyl)-HPI
(+)-2-(4-hydroxycyclohexylcarbonyl)-HPI
(−)-2-(4-hydroxycyclohexylcarbonyl)-HPI
2-(2,4-dihydroxycyclohexylcarbonyl)-HPI
2-(3,4-cis-dihydroxycyclohexylcarbonyl)-HPI, hydrate, m.p. 100°–102°
2-(3,5-dihydroxycyclohexylcarbonyl)-HPI
2-(3,4,5-trihydroxycyclohexylcarbonyl)-HPI.

EXAMPLE 37

Analogously to Example 1, 2-(4-benzyloxycarbonylaminobenzoyl)-HPI is produced from HPI and 4-(benzyloxycarbonylamino)-benzoyl chloride.

The following final products are obtained analogously with the corresponding acid halogenides:

2-(4-methoxyacetamidocyclohexylcarbonyl)-HPI
2-(4-tert.-butoxycarbonylaminocyclohexylcarbonyl)-HPI
2-(4-benzyloxycarbonylaminocyclohexylcarbonyl)-HPI
2-[4-(3,5-dimethoxybenzyl-oxycarbonyl)-aminocyclohexylcarbonyl]-HPI
2-(2-methoxyacetamidobenzoyl)-HPI
2-(2-tert.-butoxycarbonylaminobenzoyl)-HPI
2-(2-benzyloxycarbonylaminobenzoyl)-HPI
2-[2-(3,5-dimethoxybenzyl-oxycarbonyl)-aminobenzoyl]-HPI
2-(3-methoxyacetamidobenzoyl)-HPI
2-(3-tert.-butoxycarbonylaminobenzoyl)-HPI
2-(3-benzyloxycarbonylaminobenzoyl)-HPI
2-[3-(3,5-dimethoxybenzyl-oxycarbonyl)-aminobenzoyl]-HPI
2-(4-methoxyacetamidobenzoyl)-HPI, m.p. 172°
2-(4-tert.-butoxycarbonylaminobenzoyl)-HPI
2-[4-(3,5-dimethoxybenzyl-oxycarbonyl)-aminobenzoyl]-HPI
2-(1-tert.-butoxycarbonylpiperidyl-3-carbonyl)-HPI
2-(1-benzyloxycarbonylpiperidyl-3-carbonyl)-HPI
2-[1-(3,5-dimethoxybenzyl-oxycarbonyl)-piperidyl-3-carbonyl]-HPI
2-(1-benzyloxycarbonylpiperidyl-4-carbonyl)-HPI.

EXAMPLE 38

4.5 g. of 2-(1-benzyloxycarbonylpiperidyl-3-carbonyl)-HPI is hydrogenated in 100 ml. of 80% aqueous dioxane and 1 ml. of acetic acid on 300 mg. of palladium; the catalyst is filtered off, evaporated, the residue taken up in chloroform, washed with soda solution and water, evaporated, and the product is 2-(piperidyl-3-carbonyl)-HPI.

Analogously, the following compounds are produced by hydrogenolysis of the corresponding benzyloxycarbonylaminoacyl derivatives:

trans-2-(4-aminocyclohexylcarbonyl)-HPI, hydrobromide, m.p. 284°
2-(2-aminobenzoyl)-HPI, hydrobromide, m.p. 279°–280°
2-(3-aminobenzoyl)-HPI, m.p. 161°–162°
2-(4-aminobenzoyl)-HPI, m.p. 212°–213°
2-(piperidyl-4-carbonyl)-HPI, monohydrate, m.p. 146°–147°.

EXAMPLE 39

A solution of 4.3 g. of 2-(1-tert.-butoxycarbonylpiperidyl-3-carbonyl)-HPI in 80 ml. of 98% formic acid is allowed to stand for 5 hours at 20°. The mixture is then evaporated, the residue taken up in chloroform, washed with soda solution and water, and evaporated, thus obtaining 2-(piperidyl-3-carbonyl)-HPI.

EXAMPLE 40

A solution of 5.1 g. of 2-[1-(3,5-dimethoxybenzyloxycarbonyl)-piperidyl-3-carbonyl]-HPI in 100 ml. of 80% aqueous dioxane is irradiated for 2 hours with a high-pressure mercury lamp. The mixture is combined with hydrochloric acid, washed with ether, make alkaline with sodium hydroxide solution, extracted with chloroform, and evaporated, thus producing 2-(piperidyl-3-carbonyl)-HPI.

EXAMPLE 41

6.4 of 2-(4-aminobenzoyl)-HPI, 2.7 g. of salicylic aldehyde, and 100 mg. of p-toluenesulfonic acid chloride are refluxed in 150 ml. of toluene for 12 hours; the thus-liberated water is removed. The mixture is evaporated and triturated with ether, thus obtaining 2-(4-o-hydroxybenzylideneaminobenzoyl)-HPI, m.p. 196°–197° (from benzene/petroleum ether).

Analogously, 2-(4-benzylideneaminobenzoyl)-HPI is obtained with benzaldehyde.

EXAMPLE 42

3 g. of 2-(4-benzylideneaminobenzoyl)-HPI is hydrogenated in 50 ml. of methanol on 1 g. of platinum for 3 hours at 20° and under normal pressure. After the catalyst has been filtered off and the mixture evaporated, 2-(4-benzylaminobenzoyl)-HPI is obtained, m.p. 204°–205°.

Analogously, the following compounds are produced from the corresponding Schiff bases by hydrogenation:
2-(3-benzylaminocyclopentylcarbonyl)-HPI
2-(4-benzylaminocyclohexylcarbonyl)-HPI
2-(3-benzylaminobenzoyl)-HPI
2-[3-(2-hydroxybenzyl)-aminocyclopentylcarbonyl]-HPI
2-[4-(2-hydroxybenzyl)-aminocyclohexylcarbonyl]-HPI
2-[3-(2-hydroxybenzyl)-aminobenzoyl]-HPI
2-[4-(2-hydroxybenzyl)-aminobenzoyl]-HPI, m.p. 201°-202°
2-[3-(2-hydroxy-3-methoxybenzyl)-aminocyclopentylcarbonyl]-HPI
2-[4-(2-hydroxy-3-methoxybenzyl)-aminocyclohexylcarbonyl]-HPI
2-[3-(2-hydroxy-3-methoxybenzyl)-aminobenzoyl]-HPI
2-[4-(2-hydroxy-3-methoxybenzyl)-aminobenzoyl]-HPI
2-(3-carboxymethylaminocyclopentylcarbonyl)-HPI
2-(4-carboxymethylaminocyclohexylcarbonyl)-HPI
2-(3-carboxymethylaminobenzoyl)-HPI
2-(4-carboxymethylaminobenzoyl)-HPI.

Instead of using platinum during the hydrogenation, the reaction can also be conducted with Raney nickel; dioxane is used as the solvent in this case, and the hydrogenation is effected at 45° and 1-5 atmospheres.

EXAMPLE 43

Analogously to Example 38, 2-(4-aminobenzoyl)-HPI, m.p. 212°-213°, is obtained from 2-(4-benzylideneaminobenzoyl)-HPI by hydrogenation on palladium.

EXAMPLE 44

At 5°-10°, a diazonium salt solution prepared from 3.21 g. of 2-(4-aminobenzoyl)-HPI, 5 ml. of 6N hydrochloric acid, 0.7 g. of sodium nitrite, and 4 ml. of water is poured into a solution of 1.38 g. of salicylic acid in 15 ml. of 2N sodium hydroxide solution. Care is taken that the solution remains alkaline. After one-half hour, the thus-obtained product is precipitated with hydrochloric acid, filtered off, washed with water and a small quantity of ethanol, and dried, yielding 2-[4-(3-carboxy-4-hydroxyphenylazo)-benzoyl]-HPI as an orange-yellow powder; m.p. 241°-244°.

Analogously, the following final products are obtained with anisole and dimethylaniline:
2-(4-p-methoxyphenylazobenzoyl)-HPI
2-(4-p-dimethylaminophenylazobenzoyl)-HPI.

EXAMPLE 45

300 ml. of a 3.7N solution of sodium bisulfite is heated with 49 g. of cinnamic aldehyde for one-half hour to 90°. To this mixture is added 111.7 g. of 2-(4-aminobenzoyl)-HPI in 1 l. of dioxane, and the mixture is heated for 12 hours to 90°. After cooling, an extraction is carried out with chloroform; the aqueous phase is concentrated, and the product is precipitated by adding ethanol, thus obtaining the disodium salt of 2-[4-(1,3-disulfo-3-phenylpropylamino)-benzoyl]-HPI; m.p. 221°-222° (decomposition).

EXAMPLE 46

Analogously to Example 24, 2-(4-allylaminobenzoyl)-HPI is produced from 2-(4-aminobenzoyl)-HPI and allyl iodide.

The following compounds are analogously obtained:
2-(3-allylaminocyclopentylcarbonyl)-HPI
2-(4-allylaminocyclohexylcarbonyl)-HPI
2-(3-allylaminobenzoyl)-HPI.

EXAMPLE 47

Analogously to Example 5, the following final products are obtained from the corresponding amino compounds with succinic anhydride, maleic anhydride, and phthalic anhydride, respectively:
2-(4-succinylaminobenzoyl)-HPI
2-(4-maleinoylaminobenzoyl)-HPI
2-(4-phthaloylaminobenzoyl)-HPI
2-(1-succiinylpiperidyl-4-carbonyl)-HPI
2-(1-maleinoylpiperidyl-4-carbonyl)-HPI
2-(1-phthaloylpiperidyl-4-carbonyl)-HPI.

EXAMPLE 48

4.8 g. of 2-(3-cyclohexenyl-1-carbonyl)-HPI and 4 g. of osmium tetroxide are agitated overnight in 60 ml. of pyridine at 20°; then, a solution of 7 g. of sodium bisulfite in 110 ml. of water and 85 ml. of pyridine is added thereto and the mixture stirred for 30 minutes, whereupon it is extracted with methylene chloride. Drying and evaporation yield 2-(3,4-cis-dihydroxycyclohexyl-1-carbonyl)-HPI, hydrate, m.p. 100°-102°.

EXAMPLE 49

3.1 g. of 2-(3-cyclohexenyl-1-carbonyl)-HPI is hydrogenated on 300 mg. of platinum oxide in 100 ml. of methanol at 20° and under normal pressure until the reaction has ceased; the mixture is then filtered and evaporated, thus obtaining 2-cyclohexylcarbonyl-HPI, m.p. 136°-138°.

EXAMPLE 50

A solution of 3.3 g. of 2-(tetrahydrothiopyran-4-carbonyl)-HPI and 1.05 ml. of 30% aqueous hydrogen peroxide is allowed to stand overnight at 20° in 20 ml. of acetic acid; then, the mixture is evaporated and worked up with chloroform and water, yielding 2-(tetrahydrothiopyran-4-carbonyl)-HPI-S-oxide as a mixture of isomers, m.p. 175°-180°.

EXAMPLE 51

3.3 g. of 2-(tetrahydrothiopyran-4-carbonyl)-HIP and 2.5 ml. of 30% aqueous hydrogen peroxide are heated in 25 ml. of acetic acid for 2 hours to 60°; the mixture is then evaporated and worked up with chloroform and water, thus obtaining 2-(tetrahydrothiopyran-4-carbonyl)-HPI-S,S-dioxide, m.p. 253°-255° (from ethanol).

EXAMPLE 52

Under nitrogen, 35 ml. of a 0.5-molar solution of potassium tri-sec.-butyl borohydride in THF is added gradually at -70° to a solution of 4.9 g. of 2-(4-oxocyclohexylcarbonyl)-HPI in 50 ml. of absolute THF. After 3 hours, the mixture is mixed with 50 ml. of water, allowed to come to room temperature, acidified with HCl, and extracted with chloroform. The chloroform extract is purified by chromatography (silica gel/chloroform), thus obtaining pure cis-2-(4-hydroxycyclohexylcarbonyl)-HPI, m.p. 162°-163° (from isopropanol/diethyl ether).

The effective agents of Formula 1 can be processed to pharmaceutical preparations according to methods known from the literature, as demonstrated by the following examples:

EXAMPLE A

Tablets to Combat Cestodes (Adult Form)

(a) Tablets containing 500 mg. of 2-cyclohexylcarbonyl-HPI as the active ingredient are produced by processing a powder mixture of 5 kg. of 2-cyclohexylcarbonyl-HPI, 3 kg. of lactose, 1.8 kg. of corn starch, and 0.2 kg. of magnesium stearate.

(b) The same mixture can be utilized for the production of tablets containing 50, 250 and 1,000 mg. of 2-cyclohexylcarbonyl-HPI.

The tablets containing 250 and 500 mg. of 2-cyclohexylcarbonyl-HPI are preferably utilized for purposes of human medicine; all above-described tablets can be used for veterinary purposes.

EXAMPLE B

Tablets to Combat Preferably Cestode Cysticerci and/or Schistosoma

| (a) Effervescent Tablet | |
|---|---|
| Each tablet contains: | |
| 2-Cyclohexylcarbonyl-HPI | 1,000 mg. |
| Citric acid | 800 mg. |
| Sodium carbonate | 900 mg. |
| Saccharin | 5 mg. |
| Saccharose | ad 4,000 mg. |
| (b) Chewable Sugar Tablet | |
| Each tablet contains: | |
| 2-Cyclohexylcarbonyl-HPI | 2,000 mg. |
| Cellulose | 80 mg. |
| Carboxymethylcellulose sodium salt | 40 mg. |
| Coloring agent and flavoring substances | as desired |
| Saccharose | ad 4,000 mg. |

EXAMPLE C

Dragees to Combat Cestodes in Human Medicine

The dragee core contains the following ingredients:

| 2-cyclohexylcarbonyl-HPI | 250 mg. |
|---|---|
| Lactose | 150 mg. |
| Corn starch | 90 mg. |
| Magnesium stearate | 10 mg. |

The dragee coating is composed of: talc, saccharose, titanium dioxide, calcium carbonate, polyvinylpyrrolidone, methylcellulose, glycerin, magnesium oxide, lacquer.

This formulation can also be used for dragees containing 500 mg. of 2-cyclohexylcarbonyl-HPI as the active agent.

EXAMPLE D

Elixir to Combat Cestodes (Human Medicine)

The elixir is prepared by making a suspension of the following:

| 2-Cyclohexylcarbonyl-HPI | 3.5 | kg. |
|---|---|---|
| Distilled water | 2 | l. |
| Buffer | 0.1 | l. |
| Glycerin | 3 | kg. |
| Sorbitol | 3 | kg. |
| Saccharose | 53 | kg. |
| Mixture of 60% methyl p-hydroxybenzoate and 40% propyl p-hydroxybenzoate | 0.1 | kg. |
| Ethanol | 12 | l. |

The mixture is combined with coloring and flavoring agents and filled up to a volume of 100 l. with distilled water.

EXAMPLE E

Capsules for Combating Cestodes and Schistosoma for Human and Veterinary Medicine Capsules of a corresponding size are filled with a mixture of:

| 2-Cyclohexylcarbonyl-HPI | 5,000 mg. |
|---|---|
| Talc | 250 mg. |
| Magnesium stearate | 150 mg. |

Correspondingly, capsules are produced containing 1,000 mg. and 10,000 mg. of 2-cyclohexylcarbonyl-HPI.

EXAMPLE F

Injection Fluid for Purposes of Human and Veterinary Medicine

For subcutaneous administration in an oily or aqueous suspension, 15 mg.-ampoules are filled with a solution of 500 mg. of 2-cyclohexylcarbonyl-HPI in 6 ml. of water and 4 ml. of propylene glycol, with the addition of a solubilizer. The ampoules are sterilized by heat or mixed with a preservative.

Correspondingly, ampoules are produced containing 100 mg. of 2-cyclohexylcarbonyl-HPI (for small animals) and 1,000 mg. of 2-cyclohexylcarbonyl-HPI (for large animals).

EXAMPLE G

Pellets

A pulverulent mixture is prepared from equal parts by weight of 2-cyclohexylcarbonyl-HPI and lactose; this mixture is converted together with carboxymethylcellulose sodium salt in the usual manner into a uniformly granulated material having an average particle diameter of 1.5 mm.

EXAMPLE H

Premix for Purposes of Veterinary Medicine, Suitable for Mixing with a Feed Material as the Vehicle to Obtain a Medical Animal Food (a) 25% Premix (preferably for larger animals):
25 kg. of 2-cyclohexylcarbonyl-HPI is mixed with 75 kg. of fine bran (wheat middlings) and/or lactose.

(b) 5% Premix (preferably for smaller animals):
5 kg of 2-cyclohexylcarbonyl-HPI are processed analogously to (a).

(c) Example for the use of a premix produced according to (a) for combating Moniezia genera in the cattle intestine.

To obtain a suitable medical feed, 1 kg. of the premix produced according to (a) is combined with 9 kg. of a conventional feed concentrate. To combat Moniezia infestation, 400 g. of this medical feed, containing 10,000 mg. of 2-cyclohexylcarbonyl-HPI, is administered to adult cattle, per head.

Analogously to Examples A–H, it is also possible to process, in place of 2-cyclohexylcarbonyl-HPI, the other active agents of Formula 1 or the physiologically acceptable salts thereof to obtain pharmaceutical preparations.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical composition comprising, in admixture with a pharmaceutically acceptable carrier, an anthelmintically effective amount per unit dosage of a compound of the formula

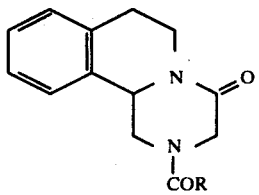

wherein R is phenyl mono-substituted in the o-position by fluorine or in the m- or p-position by fluorine, chlorine, nitro, hydroxy, amino, formylamino, acetylamino, pentanoylamino, hexanoylamino, octanoylamino, oleoylamino, methoxyacetylamino, methylamino, dimethylamino or allylamino, or a physiologically acceptable acid addition salt thereof.

2. A composition of claim 1 wherein the compound is, 2-(2-fluorobenzoyl)-4-oxo-1,2,3,6,7,11b-hexahydro-4H-pyrazino[2,1-a]isoquinoline.

3. A composition of claim 1 wherein the compound is, 2-(3-fluorobenzoyl)-4-oxo-1,2,3,6,7,11b-hexahydro-4H-pyrazino[2,1-a]isoquinoline.

4. A composition of claim 1 wherein the compound is, 2-(4-fluorobenzoyl)-4-oxo-1,2,3,6,7,11b-hexahydro-4H-pyrazino[2,1-a]isoquinoline.

5. A composition of claim 1 wherein the compound is, 2-(3-aminobenzoyl)-4-oxo-1,2,3,6,7,11b-hexahydro-4H-pyrazino[2,1-a]isoquinoline.

6. A composition of claim 1 wherein the compound is, 2-(4-aminobenzoyl)-4-oxo-1,2,3,6,7,11b-hexahydro-4H-pyrazino[2,1-a]isoquinoline.

7. A composition of claim 1 wherein the compound is, 2-(3-formamidobenzoyl)-4-oxo-1,2,3,6,7,11b-hexahydro-4H-pyrazino[2,1-a]isoquinoline.

8. A composition of claim 1 wherein the compound is, 2-(4-formamidobenzoyl)-4-oxo-1,2,3,6,7,11b-hexahydro-4H-pyrazino[2,1-a]isoquinoline.

9. A composition of claim 1 wherein the compound is, 2-(4-nitrobenzoyl)-4-oxo-1,2,3,6,7,11b-hexahydro-4H-pyrazinl[2,1-a]isoquinoline.

10. A method of treating cestode and trematode infestations which comprises administering to an animal infested with cestodes or trematodes an anthelmintically effective amount of a compound of the formula

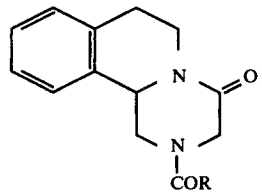

wherein R is phenyl mono-substituted in the o-position by fluorine or in the m- or p-position by fluorine, chlorine, nitro, hydroxy, amino, formylamino, acetylamino, pentanoylamino, hexanoylamino, octanoylamino, oleoylamino, methoxyacetylamino, methylamino, dimethylamino or allylamino, or a physiologically acceptable acid addition salt thereof.

11. A composition of claim 1 wherein the compound is, 2-(4-methylaminobenzoyl)-4-oxo-1,2,3,6,7,11b-hexahydro-4H-pyrazino[2,1-a]isoquinoline.

12. A composition of claim 1 wherein the compound is, 2-(4-dimethylaminobenzoyl)-4-oxo-1,2,3,6,7,11b-hexahydro-4H-pyrazino[2,1-a]isoquinoline.

13. A composition of claim 1 wherein the compound is, 2-(3-acetamidobenzoyl)-4-oxo-1,2,3,6,7,11b-hexahydro-4H-pyrazino[2,1-a]isoquinoline.

14. A composition of claim 1 wherein the compound is, 2-(4-acetamidobenzoyl)-4-oxo-1,2,3,6,7,11b-hexahydro-4H-pyrazino[2,1-a]isoquinoline.

15. A composition of claim 1 wherein the compound is, 2-(3-methoxyacetamidobenzoyl)-4-oxo-1,2,3,6,7,11b-hexahydro-4H-pyrazino[2,1-a]isoquinoline.

16. A composition of claim 1 wherein the compound is, 2-(4-methoxyacetamidobenzoyl)-4-oxo-1,2,3,6,7,11b-hexahydro-4H-pyrazino[2,1-a]isoquinoline.

* * * * *